United States Patent
Weinmann (12)

(10) Patent No.: US 6,518,052 B1
(45) Date of Patent: Feb. 11, 2003

(54) HUMAN HOMOLOGUE OF YEAST HELICASE AND USES THEREOF

(75) Inventor: Roberto Weinmann, Princeton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/425,335

(22) Filed: Oct. 22, 1999

(51) Int. Cl.[7] .............................. C12N 9/14; C07H 21/04

(52) U.S. Cl. ..................... 435/195; 435/183; 435/194; 435/252.3; 435/320.1; 435/325; 536/23.2; 536/23.1; 536/25.5

(58) Field of Search ............................ 435/194, 183, 435/195, 325, 252.3, 320.1; 536/23.2, 23.1, 23.5

(56) References Cited

U.S. PATENT DOCUMENTS 5,466,576 A   11/1995   Schulz et al. ................... 435/6
5,770,422 A   6/1998    Collins ......................... 435/194

FOREIGN PATENT DOCUMENTS

WO   WO 9938972   5/1999

OTHER PUBLICATIONS

Foury et al. Cloning and sequencing of the PIF gene involved in repair and recombination of yeast mitochondrial DNA, European Journal of Molecular Biology vol. 6 (5): 1441–1449, 1987.*
Matsuda et al. C. elegans mRNA for PIF1, complete cds, EMBL Database, Accession No. AB015041, Jun. 1998.*
Schulz, V.P., et al., EMBL database, Accession No. AF108138 Heidelberg, FRG. Jul. 1999.
Matsuda, T., EMBL database, Accession No. AB015041 Heidelberg, FRG. Jun. 1998.
Matsuda, T., EMBL database, Accession No. 061298 Heidelberg, FRG. Aug. 1998.
Shay et al., Exp. Cell Res., 1991, 196:33.
Hahn et al., Nature, 1999, 400:464–468.
Griffith et al., Cell, 1999, 97:503–514.
Foury et al., EMBO J., 1987, 6:1441–1449.
Johnston, Science, 1994, 265:2077–2082.
Lahaye et al., EMBO J., 1991, 10:997.
J.–Q. Zhou et al., "Pif1p Helicase, a Catalytic Inhibitor of Telomerase in Yeast", Science, Aug. 2000, No. 289, pp. 771–774.

* cited by examiner

Primary Examiner—Rebecca E. Prouty
Assistant Examiner—Richard Hutson
(74) Attorney, Agent, or Firm—Christopher A. Klein; Joan E. Switzer

(57) ABSTRACT

The present invention provides a nucleic acid and amino acid sequence of a human Pif-1 type helicase. The invention also provides methods of screening for compounds that modulate the activity of human Pif-1 type helicase, as well as methods for affecting viability of a cell by contacting the cell with a human Pif-1 helicase modulator. Such contacting specifically increases or decreases the specific activity of the human helicase in the cell, and may affect its viability, by affecting telomere length regulatory processes.

17 Claims, 10 Drawing Sheets

```
   1  ATGCTCTCGG GCATAGAGGC GGCGGCAGGG GAATATGAGG ACTCGGAGCT
  51  GCGGTGCCGC GTGGCTGTGG AGGAGCTGAG CCCGGGCGGG CAGCCGCGAA
 101  GGCGCCAGGC CCTGCGCACC GCGGAGCTGA GCCTGGGTCG CAACGAGCGC
 151  CGCGAGTTGA TGCTGCGGCT GCAAGCGCCA GGGCCCGCGG GCGGCCGCG
 201  CTGCTTCCCT CTGCGCGCCG CGCGCCTCTT CACGCGTTTC GCCGAGGCCG
 251  GGCGCAGCAC CCTGCGGCTC CCCGCCCACG ACACCCCGG GGCCGGCGCA
 301  GTGCAGCTGC TGCTCTCGGA CTGCCCCCA GACCGCCTGC GCCGCTTCCT
 351  GCGCACATTG CGCCTCAAGC TGGCTGCGGC CCCGGGTCCC GGGCCGGCCT
 401  CCGCCCGAGC GCAGCTGCTG GGCCCGCGGC CCGCGACTT CGTCACCATC
 451  AGCCCTGTGC AGCCCGAGGA GCGGCGGCTC AGGGCGGCCA CCCGGGTTCC
 501  GGACACTACG CTGGTGAAGC GGCCTGTGGA GCCCCAGGCT GGGGCCGAGC
 551  CTAGCACAGA AGCCCCAAGG TGGCCCCTGC CTGTGAAGAG GCTGAGCTTG
 601  CCCTCCACCA AGCCACAGCT TTCTGAGGAA CAGGCTGCTG TGCTGAGGGC
 651  CGTCCTGAAA GGCCAGAGCA TCTTCTTCAC TGGGAGTGCA GGCACTGTGG
 701  CCACTGCCAG CACTGGGGTG GCAGCCTGCC ACATCGGGGG CACCACCCTC
 751  CATGCCTTTG CAGGCATCGG CTCAGGCCAG GCTCCTCTAG CCCAGTGTGT
 801  GGCCCTGGCC CAAAGGCCAG GCGTGCGGCA GGGCTGGCTG AACTGCCAGC
 851  GGTTGGTCAT TGACGAGATC TCAATGGTGG AGGCAGACCT GTTTGACAAA
 901  CTGGAGGCCG TGGCCAGAGC TGTCCGGCAG CAGAACAAGC CATTCGGAGG
 951  GATCCAGCTC ATCATCTGTG GGACTTTCT GCAGCTGCCA CCTGTGACCA
1001  AGGGCTCCCA GCCCCACGG TTCTGCTTCC AGTCCAAGAG CTGGAAGAGG
1051  TGTGTGCCAG TGACCCTGGA GCTGACCAAG GTGTGGAGGC AGGCAGACCA
1101  GACCTTCATC TCTCTACTGC AGGCCGTGAG GCTAGGCAGG TGTTCAGATG
1151  AGGTGACCCG CCAGCTCCAG GCCACAGCTT CCCACAAGGT GGGGCGAGAT
1201  GGGATTGTGG CCACGAGGCT CTGCACCCAC CAGGATGATG TGGCCCTCAC
1251  CAACGAGAGG CGGCTTCAGG AGCTGCCAGG TAAGGTACAC AGATTTGAGG
1301  CTATGGACAG CAACCCTGAG CTGGCCAGTA CCCTGGATGC CCAGTGTCCT
1351  GTTAGCCAGC TCCTTCAACT AAAGCTGGGG GCCCAGGTGA TGCTGGTGAA
1401  AAACTTATCG GTGTCTCGGG GCCTGGTGAA TGGTGCCCGA GGGGTGGTAG
1451  TTGGGTTCGA GGCAGAAGGG AGAGGGCTAC CCCAGGTGCG GTTCCTGTGT
1501  GGAGTCACTG AGGTCATCCA CGCTGACCGC TGGACGGTGC AGGCCACCGG
1551  GGGCCAGCTC CTCAGTCGGC AGCAGCTGCC CCTCCAGCTG GCCTGGGCGA
1601  TGTCCATCCA AAGAGCCAA GGCATGACCC TGGATTGTGT GGAGATTTCT
1651  CTGGGCCGTG TGTTTGCCAG TGGCCAGGCC TATGTGGCCC TTTCTCGGGC
1701  CCGCAGCCTG CAGGGCCTAC GTGTGCTGGA CTTTGACCCC ATGGCGGTTC
1751  GCTGTGACCC CCGTGTGCTG CACTTCTATG CCACCCTGCG GCGGGGCAGG
1801  AGCCTCAGTC TGGCTGCAGA AGGGAGAGGC AATGAAGACA GGTGCTCCGG
1851  AAGCAGCATC AGGGCTCTTG GAGGGACTG GTGGGACTC AGGCTGGGTG
1901  CAGCCTCCAA ACAGAGAACG GAACTTAGGT GTGTCTCTAC AGCTAGGCCC
1951  AGCCTAGCCC AGCCCAGAAC AAACACCCTT CAGAGCCTAA CCAAAGAACA
2001  TAAGCTGCAA AATGTGCACC CATATTTTAA GCTGCTTTTT CAGGGGATAA
2051  ATAGTGTTTG GGACATTGA AATGGATGTT CTCAGGTTGT ATTTATTTCG
2101  GACAAATAAA CTAGAGAATT GTGTAAAAAA
```

FIG. 1

```
      ATGCTCTCGGGCATAGAGGCGGCGGCAGGGGAATATGAGGACTCGGAGCTGCGGTGCCGC
  1   ---------+---------+---------+---------+---------+---------+ 60
      m  l  s  g  i  e  a  a  a  g  e  y  e  d  s  e  l  r  c  r   -

GTGGCTGTGGAGGAGCTGAGCCCGGGCGGGCAGCCGCGAAGGCGCCAGGCCCTGCGCACC
 61   ---------+---------+---------+---------+---------+---------+ 120
      v  a  v  e  e  l  s  p  g  g  q  p  r  r     r  q  a  l  r  t  -

GCGGAGCTGAGCCTGGGTCGCAACGAGCGCCGCGAGTTGATGCTGCGGCTGCAAGCGCCA
121   ---------+---------+---------+---------+---------+---------+ 180
      a  e  l  s  l  g  r  n  e  r     r  e  l  m  l  r  l  q  a  p  -

GGGCCCGCGGGGCGGCCGCGCTGCTTCCCTCTGCGCGCCGCGCGCCTCTTCACGCGTTTC
181   ---------+---------+---------+---------+---------+---------+ 240
      g  p  a  g  r  p  r  c  f  p  l  r  a  a  r  l  f  t  r  f   -

GCCGAGGCCGGGCGCAGCACCCTGCGGCTCCCCGCCCACGACACCCCCGGGGCCGGCGCA
241   ---------+---------+---------+---------+---------+---------+ 300
      a  e  a  g  r  s  t  l  r  l  p  a  h  d  t  p  g  a  g  a   -

GTGCAGCTGCTGCTCTCGGACTGCCCCCCAGACCGCCTGCGCCGCTTCCTGCGCACATTG
301   ---------+---------+---------+---------+---------+---------+ 360
      v  q  l  l  l  s  d  c  p  p  d  r  l  r     r  f  l  r  t  l  -

CGCCTCAAGCTGGCTGCGGCCCCGGGTCCCGGGCCGGCCTCCGCCCGAGCGCAGCTGCTG
361   ---------+---------+---------+---------+---------+---------+ 420
      r  l  k  l  a  a  a  p  g  p  g  p  a  s  a  r  a  q  l  l   -

GGCCCGCGGCCCCGCGACTTCGTCACCATCAGCCCTGTGCAGCCCGAGGAGCGGCGGCTC
421   ---------+---------+---------+---------+---------+---------+ 480
      g  p  r  p  r  d  f  v  t  i  s  p  v  q  p  e  e  r     r  l  -

AGGGCGGCCACCCGGGTTCCGGACACTACGCTGGTGAAGCGGCCTGTGGAGCCCCAGGCT
481   ---------+---------+---------+---------+---------+---------+ 540
      r  a  a  t  r  v  p  d  t  t  l  v  k  r  p  v  e  p  q  a   -

GGGGCCGAGCCTAGCACAGAAGCCCCAAGGTGGCCCCTGCCTGTGAAGAGGCTGAGCTTG
541   ---------+---------+---------+---------+---------+---------+ 600
      g  a  e  p  s  t  e  a  p  r  w  p  l  p  v  k  r  l  s  l   -
```

FIG. 2A

```
     CCCTCCACCAAGCCACAGCTTTCTGAGGAACAGGCTGCTGTGCTGAGGGCCGTCCTGAAA
601  ---------+---------+---------+---------+---------+---------+ 660
      p  s  t  k  p  q  l  s  e  e  q  a  a  v  l  r  a  v  l  k  -

GGCCAGAGCATCTTCTTCACTGGGAGTGCAGGCACTGTGGCCACTGCCAGCACTGGGGTG
661  ---------+---------+---------+---------+---------+---------+ 720
      g  q  s  i  f  f  t  g  s  a  g  t  v  a  t  a  s  t  g  v  -

GCAGCCTGCCACATCGGGGGCACCACCCTCCATGCCTTTGCAGGCATCGGCTCAGGCCAG
721  ---------+---------+---------+---------+---------+---------+ 780
      a  a  c  h  i  g  g  t  t  l  h  a  f  a  g  i  g  s  g  q  -

GCTCCTCTAGCCCAGTGTGTGGCCCTGGCCCAAAGGCCAGGCGTGCGGCAGGGCTGGCTG
781  ---------+---------+---------+---------+---------+---------+ 840
      a  p  l  a  q  c  v  a  l  a  q  r  p  g  v  r  q  g  w  l  -

AACTGCCAGCGGTTGGTCATTGACGAGATCTCAATGGTGGAGGCAGACCTGTTTGACAAA
841  ---------+---------+---------+---------+---------+---------+ 900
      n  c  q  r  l  v  i  d  e  i  s  m  v  e  a  d  l  f  d  k  -

CTGGAGGCCGTGGCCAGAGCTGTCCGGCAGCAGAACAAGCCATTCGGAGGGATCCAGCTC
901  ---------+---------+---------+---------+---------+---------+ 960
      l  e  a  v  a  r  a  v  r  q  q  n  k  p  f  g  g  i  q  l  -

ATCATCTGTGGGGACTTTCTGCAGCTGCCACCTGTGACCAAGGGCTCCCAGCCCCCACGG
961  ---------+---------+---------+---------+---------+---------+ 1020
      i  i  c  g  d  f  l  q  l  p  p  v  t  k  g  s  q  p  p  r  -

TTCTGCTTCCAGTCCAAGAGCTGGAAGAGGTGTGTGCCAGTGACCCTGGAGCTGACCAAG
1021 ---------+---------+---------+---------+---------+---------+ 1080
      f  c  f  q  s  k  s  w  k  r  c  v  p  v  t  l  e  l  t  k  -

GTGTGGAGGCAGGCAGACCAGACCTTCATCTCTCTACTGCAGGCCGTGAGGCTAGGCAGG
1081 ---------+---------+---------+---------+---------+---------+ 1140
      v  w  r  q  a  d  q  t  f  i  s  l  l  q  a  v  r  l  g  r  -

TGTTCAGATGAGGTGACCCGCCAGCTCCAGGCCACAGCTTCCCACAAGGTGGGGCGAGAT
1141 ---------+---------+---------+---------+---------+---------+ 1200
      c  s  d  e  v  t  r  q  l  q  a  t  a  s  h  k  v  g  r  d  -

GGGATTGTGGCCACGAGGCTCTGCACCCACCAGGATGATGTGGCCCTCACCAACGAGAGG
1201 ---------+---------+---------+---------+---------+---------+ 1260
      g  i  v  a  t  r  l  c  t  h  q  d  d  v  a  l  t  n  e  r  -
```

FIG. 2B

```
          CGGCTTCAGGAGCTGCCAGGTAAGGTACACAGATTTGAGGCTATGGACAGCAACCCTGAG
1261      ---------+---------+---------+---------+---------+---------+ 1320
           r  l  q  e  l  p  g  k  v  h  r  f  e  a  m  d  s  n  p  e  -

CTGGCCAGTACCCTGGATGCCCAGTGTCCTGTTAGCCAGCTCCTTCAACTAAAGCTGGGG
1321      ---------+---------+---------+---------+---------+---------+ 1380
           l  a  s  t  l  d  a  q  c  p  v  s  q  l     l  q  l  k  l  g  -

GCCCAGGTGATGCTGGTGAAAAACTTATCGGTGTCTCGGGGCCTGGTGAATGGTGCCCGA
1381      ---------+---------+---------+---------+---------+---------+ 1440
           a  q  v  m  l  v  k  n  l  s  v  s  r  g  l  v  n  g  a  r  -

GGGGTGGTAGTTGGGTTCGAGGCAGAAGGGAGAGGGCTACCCCAGGTGCGGTTCCTGTGT
1441      ---------+---------+---------+---------+---------+---------+ 1500
           g  v  v  v  g  f  e  a  e  g  r  g  l  p  q  v  r  f  l  c  -

GGAGTCACTGAGGTCATCCACGCTGACCGCTGGACGGTGCAGGCCACCGGGGGCCAGCTC
1501      ---------+---------+---------+---------+---------+---------+ 1560
           g  v  t  e  v  i  h  a  d  r  w  t  v  q  a  t  g  g  q  l  -

CTCAGTCGGCAGCAGCTGCCCCTCCAGCTGGCCTGGGCGATGTCCATCCACAAGAGCCAA
1561      ---------+---------+---------+---------+---------+---------+ 1620
           l  s  r  q  q  l  p  l  q  l  a  w  a  m  s  i  h  k  s  q  -

GGCATGACCCTGGATTGTGTGGAGATTTCTCTGGGCCGTGTGTTTGCCAGTGGCCAGGCC
1621      ---------+---------+---------+---------+---------+---------+ 1680
           g  m  t  l  d  c  v  e  i  s  l  g  r  v  f  a  s  g  q  a  -

TATGTGGCCCTTTCTCGGGCCCGCAGCCTGCAGGGCCTACGTGTGCTGGACTTTGACCCC
1681      ---------+---------+---------+---------+---------+---------+ 1740
           y  v  a  l  s  r  a  r  s  l  q  g  l  r  v  l  d  f  d  p  -

ATGGCGGTTCGCTGTGACCCCCGTGTGCTGCACTTCTATGCCACCCTGCGGCGGGGCAGG
1741      ---------+---------+---------+---------+---------+---------+ 1800
           m  a  v  r  c  d  p  r  v  l  h  f  y  a  t  l  r  r  g  r  -

AGCCTCAGTCTGGCTGCAGAAGGGAGAGGCAATGAAGACAGGTGCTCCGGAAGCAGCATC
1801      ---------+---------+---------+---------+---------+---------+ 1860
           s  l  s  l  a  a  e  g  r  g  n  e  d  r  c  s  g  s  s  i  -
```

FIG. 2C

```
                AGCCTCAGTCTGGCTGCAGAAGGGAGAGGCAATGAAGACAGGTGCTCCGGAAGCAGCATC
     1801       ------------+---------+---------+---------+---------+---------+ 1860
                 s  l  s  l  a  a  e  g  r  g  n  e  d  r  c  s  g  s  s  i  -

_____STS SHGC-13832_____
                AGGGCTCTTGGAGGG GACTGGTGGGGACTCAGGCTGGGTGCAGCCTCCAAACAGAGAACG
     1861       ------------+---------+---------+---------+---------+---------+ 1920
                 r  a  l  g  g  d  w  w  g  l  r  l  g  a  a  s  k  q  r  t  -

_____STS SHGC-13832_____
                GAACTTAGGTGTGTCTCTACAGCTAGGCCCAGCCTAGCCCAGCCCAGAACAAACACCCTT
     1921       ------------+---------+---------+---------+---------+---------+ 1980
                 e  l  r  c  v  s  t  a  r  p  s  l  a  q  p  r  t  n  t  l  -

_____STS SHGC-13832_____
                CAGAGCCTAACCAAAGAACATAAGCTGCAAAATGTGCACCCATATTTTAAGCTGCTTTTT
     1981       ------------+---------+---------+---------+---------+---------+ 2040
                 q  s  l  t  k  e  h  k  l  q  n  v  h  p  y  f  k  l  l  f  -

_____STS SHGC-13832_____
                CAGGGGATAAATAGTGTTTGGGGACATTGAAATGGATGTTCTCAGGTTGTATTTATTTCG
     2041       ------------+---------+---------+---------+---------+---------+ 2100
                 q  g  i  n  s  v  w  g  h  *

__STS SHGC-13832_____ polyA tail
                GACAAATAAACTAGAGAATTGTGTAAAAAA
     2101       ------------+---------+---------+ 2130
```

FIG. 2D

```
                    1                                                                          50
Human               .......... .......... Ml....S... ..........Gi eaaageye..
C. elegans          .......... .......... Ms.kslqt.. ..........de NggvSesP..
yeast               .......... ........mPk wl.R..S... ..........tl NhiiprRP..
yeast homolog       .......... .......... MF.R..S... ..Ha...SGn kkqwSkRs..
RRM3, S. pombe      mfscqslykf shsfrkriPv MFqRaqqkss llHtqneSsh qpslnklggf
Consensus           ---------- --------p- mf-r--s--- --h----sg- n---s-rp--

51                                                                        100
Human               .dseLrcrvA veelSpggQp rrrQ...alr tAelslGrNe RrelmLr.Lq
C. elegans          SNCtycytle cSlriestss ikkktpissk SAImtvGrNa qrkihLqiel
yeast               fiCSfNsfll lknvShakls FSmsSrGfrs nnfiqAqlkh psIlSkEdLD
yeast homolog       SNgStpaasA sgShayrQQt lSSffmGcgk k.saaAskNs ttIidLEsgD
RRM3, S. pombe      SsaSLNfnss rSStnddQQt FSSQSdnlps SpItlpakrg RsaaSLkqLD
Consensus           sncsln---a -ss-s--qq- fssqs-g--- sai--ag-n- r-i-sle-ld 101                                                                       150
Human               apGpag...r PrCfpLraar LftrFa.Eag rstlrlpahd tPgagavqLl
C. elegans          kTtatg...q Pavvcydvtd avvhlqs.vA NGkctvE... iPslsLmfqM
yeast               llsdsddwee PdCiqLEtek qekKiiTdIh kedpvDk... .kpmrdKNvM
yeast homolog       .eGnrn.ita PprPrLirnn ssSlFS..qs qGsfgDd... DPDaefKkLv
RRM3, S. pombe      nTvgfd.vsk PslPvfEnsg LgSKySTEIA NGvyiDEndf DdDllLeNdi
Consensus           -tg------- P-cp-le--- l-skfsteia ng---de--- dpd--lknlm 151                                                                       200
Human               lsdCpPd.r. .......... .LrrFlrtlR lklaaapgpg p...AS..Ar
C. elegans          fn.CaPR.k. .......... .LnvFmkSlq akldImkmeK S...piSavp
yeast               n..fInkdS. P......... .Lswndmfkp SiiqppqLis e...nS....
yeast homolog       D...vPR... .......... .LnSyKkSsR SlsmtssLHK t...AS..AS
RRM3, S. pombe      DqkpIPwsSs Piehtkltks mLsSeKrSkn hlskIyedHt SekgASSviS
Consensus           d--cipr-s- p--------- -L-sfk-s-r s---i--lhk s---ass-as 201                                                                       250
Human               aQllgp...R pRdfv.TiSP VqP.....eE rrlrAatr.. .vp.Dtt...
C. elegans          rQfSRppavf SvlsPlTiSe mRkvkkLrep Salarpskea Ttpkrrtssm
yeast               fdQSsq..Kk SRstg.fknP lRP..aLkkE SSfdelqN.n sisqerSlem
yeast homolog       ttQktyhfde deTLr.evts Vks...nsrq lSftstIN.. .ie.DsSmKl
RRM3, S. pombe      sniaRqgiKR SRTLPwavdP yRygdpdpkr tStsAdIsqh TvsnDsSnKl
Consensus           -qqsr---kr srtlp-t-sp vrp---l--e ss--a-in-- t---d-s-k-

251                                                                       300
Human               .......... LvKR...... ..pvepqaga ePSteAPrwP lpVkrL.S..
C. elegans          nllag....g LenR....im nrsiglKrTT sfarddreka eTlvsLKSfk
yeast               iNe.n..... ekKk....mq fgekIavlTq rPSftelqnd qddSNLnphN
yeast homolog       Std.S...er pAKR..SKp. SmefqglKlT VPkkikPllr kTVSNmdSmN
RRM3, S. pombe      SNgrSsslds LAKkrmSKsk StpqIsKKfs VPlnsAsksP igsSlfKtsd
Consensus           sn--s----- lakr--sk-- s---i-kktt vps--ap--p -tvsnlks-n nucleotide binding motif A (P-loop)
                    301                                                 /‾‾‾‾‾‾‾‾\            350
Human               .lpstkP..Q LSeEQaaVlR a.VlKgqSIF FTGSAGT... ..........
```

FIG. 3A

```
C. elegans      dapAiSerIQ  LSDEQksVvR  cVinsrtSvF  FTGSAGTGKS  ViLRrIIEmL
yeast           gvkvkiP.Ic  LSkEQesiik  L.aEnghnIF  yTGSAGTGKS  ilLRemIkVL
yeast homolog   hRsASSP.vv  LtmEQerVvn  LiVkKrtnvF  yTGSAGTGKS  ViLqtIIrqL
RRM3, S. pombe  sRkkSvPsIf  LSDEQkrild  mVVEqqhSIF  FTGSAGTGKS  VlLRkIIEVL
Consensus       -r-assp-iq  LsdEQ--v-r  lvvek--siF  fTGSAGTgks  v-lr-iievl
```

```
                351                                                    400
Human           ..va......  ...TASTGvA  AChIGGtTLH  aFAGIGsGqa  plaQcValaQ
C. elegans      pagn......  tyiTAaTGvA  AsqIGGITLH  aFcGfryeNs  TpeQclKqvl
yeast           KgiYGrEn..  VAvTASTGLA  ACNIGGITiH  sFAGI.LGkg  daDkLyKKvg
yeast homolog   sSlYGKES..  iAiTASTGLA  AvtIGGsTLH  kwsGIGiGNk  TiDQLVKKiQ
RRM3, S. pombe  KSkYrKqSdr  VAvTASTGLA  ACNIGGvTLH  sFAGvGLare  svDlLVsKik
Consensus       ks-ygkes--  va-TAsTGlA  AcnIGGiTlH  -faGiglgn-  t-dqlvkk-q
``` nucleotide binding motif B

```
                401                                            /        450
Human           R..pgvrqgW  LNcqrLvIDE  ISMVeAdLfD  KLEaVARavR  qqnKPFGGIQ
C. elegans      R.QnhmvRqW  kqcshLIIDE  ISMiDrdffe  aLEyVARtvR  nNDKPFGGIQ
yeast           RrsrKhlRRW  eNigaLvvDE  ISMlDAeLlD  KLdfiARkIR  KNhqPFGGIQ
yeast homolog   s.QKdllaaW  rytkVLIIDE  ISMVDgnLlD  KLEqiARrIR  KNDdPFGGIQ
RRM3, S. pombe  k.nKKcvnRW  LrtrVLIIDE  vSMVDAeLmD  KLEeVARvIR  KdsKPFGGIQ
Consensus       r-qkk--rrW  ln--vLiiDE  iSMvda-l-d  kLe-vAR-iR  kndkPFGGIQ
```

```
                451 \                                                   500
Human           LIicGDFlQL  PPVtKgsqPP  ..rFCFqSks  WKRCvpvrle  LTKVwRQa.D
C. elegans      LIiTGDFFQL  PPVSKD.EP.  ...vFCFESeA  WsRCiQKTIv  LknVkRQn.D
yeast           LIfcGDFFQL  PPVSKDpnrP  .tKFaFESkA  WKegvkmTIm  LqKVFRQrgD
yeast homolog   LvlTGDFFQL  PPVaKkdEhn  vvKFCFESem  WKRCiQKTIl  LTKVFRQq.D
RRM3, S. pombe  LvlTGDFFQL  PPVpengke.  .sKFCFESqt  WKsaldfTIg  LThVFRQk.D
Consensus       Li-tGDFfQL  PPVskd-epp  --kFcFeS-a  Wkrc-qkTi-  LtkVfRQ---
```

```
                501                                                     550
Human           qtFIslLqAV  RLGrcsDEvt  Rqlqatashk  vgrDGIvaTr  LcThqDdVal
C. elegans      NvFvKiLNnV  RvGKcdfkSA  dilKessknq  f.pssvIPTk  LcThsDdadR
yeast           vKFIemLNrm  RLGnidDEte  RefKkLsRpl  p.dDeIIPaE  LysTRmEVER
yeast homolog   NKlIdiLNAi  RyGeltvdiA  ktirnLnRdI  dYaDGIaPTE  LyaTRrEVEl
RRM3, S. pombe  eeFvKmLNel  RLGKlsDESv  RkfKvLnRtI  eYeDGllPTE  LfpTRyEVER
Consensus       nkfik-Lnav  RlGk--desa  r--k-l-r-i  -y-dgiipte  L-ttrdever
```

```
                551                                                     600
Human           tNerRLQeLP  GkVHrFeAmD  SnPE....La  stLdaqCpvs  qlLqLKlGAQ
C. elegans      iNsSsiettq  GDakTFhAyD  desfd....t  h.akartlAq  KkLVLKVGAQ
yeast           aNnSRLskLP  GqVHifnAID  gGaleDeELk  eRLlqnflAP  KeLhLKVGAQ
yeast homolog   SNvkkLQsLP  GDlyeFkAvD  naPER...yq  aiLdsslmve  KvvaLKedAQ
RRM3, S. pombe  SNdmRmQqin  qnpvTFtAID  SGtvRDkEfr  dRLlqgCmAP  atLVLKVnAQ
Consensus       sN-srlq-lp  gdvhtF-AiD  sgperd-el-  -rl----c-ap  k-lvlkvgAQ
```

FIG. 3B

```
                       601                                                            650
Human           VMLvKN...l  svsrGlvnga  rGvVvg....  ..........  ..........
C. elegans      VMLiKN...i  dvikGlcngs  rGFVek....  ..........  ..........
yeast           VMmvKN.lDa  tLVNGSLGKV  ieFmDpetyf  cyealtndps  mppeklETwa
yeast homolog   VMmlKNkpDv  eLVNGSLGKV  lfFVtes...  ..........  lvvkmkEiYk
RRM3, S. pombe  VMLiKN.iDd  qLVNGSLGKV  iGFiDd....  ..........  ......ETYq
Consensus       VMl-KN--d-  -lvnGslgkv  -gfvd-----  ----------  ------ety- 651                                                            700
Human           ..........  ..........  ..........  ..FEaEg...  ..........
C. elegans      ..........  ..........  ..........  ..Fseng...  ..........
yeast           enpsKlkAaM  ereqsdgees  avaSRkssvk  egFaKsdige  pvspLDsSvF
yeast homolog   iv..ddevvM  dmRl......  ..vSR..vig  NpllKEsk..  .efrqDlnar
RRM3, S. pombe  me..KkdAeM  qgR.......  ..........  NaFEyds...  ....LDiSpF
Consensus       ----k--a-m  --r-------  ---sr-----  n-feke----  ----ld-s-f 701                                                            750
Human           ..........  ..........  ..........  ....RglPqV  RFlcG.....
C. elegans      ..........  ..........  ..........  ......nPmi  RFvsq...ad
yeast           Dfmkrvktdd  evvleniKRK  eqLmqtihqn  SagKRrLPLV  RFKas.dmst
yeast homolog   pLar......  ......leRl  KiLinyavKi  SphKeKfPyV  RwtvGkNkyi
RRM3, S. pombe  DLpd......  ......vKqK  KykliamrKa  SstaiKwPLV  RFKlp.Ngge
Consensus       dl--------  -------krk  k-l-----k-  s--krklPlv  Rfk-g-n---

751                                                            800
Human           vTeVihadRW  tvqatggq.L  LSRqQLPLqL  AWAmSIHKSQ  GmTLDcVeis
C. elegans      asIeirRskf  svrIPgsdap  LiRrQLPLqL  AWAiSIHKSQ  GmTLDcaeis
yeast           RmvlVepEdW  aIEdenekpL  vSRvQLPLmL  AWslSIHKSQ  GQTLpkVKVD
yeast homolog   helmVp.ERf  pIdIPrenVg  LeRtQiPLmL  cWAlSIHKaQ  GQTiqrlKVD
RRM3, S. pombe  RTIVVqREtW  nIElPngeVq  aSRsQiPLiL  AyAiSIHKaQ  GQTLDrVKVD
Consensus       rtivv-rerw  -ieip---vl  lsR-QlPL-L  Awa-SIHKsQ  GqTld-vkvd DNA Binding region
                       801      /‾‾‾‾‾‾‾‾‾‾‾‾‾‾‾‾‾‾‾‾\                                850
Human           LgRVFasGQA  YVALSRArSL  qGLrVLdFDP  maVRcdPrVl  hFYaTLrrgr
C. elegans      LeRVFadGQA  YVALSRArSL  aairiigFDa  scVRAnsKVI  DFYKsiEaec
yeast           LrRVFEKGQA  YVALSRAvSr  EGLQVLNFDr  trikAhqKVI  DFYlTLsSae
yeast homolog   LrRiFEaGQv  YVALSRAvtm  dtLQVLNFDP  gKiRtnerVk  DFYKrLEtlk
RRM3, S. pombe  LgRVFEKGQA  YVALSRAttq  EGLQVLNFsP  aKVmAhPKVv  qFYKqLaSvn
Consensus       L-RvFekGQa  YVALSRA-sl  eglqvlnFdp  -kvra-pkvi  dFYktles--

851                                                            900
Human           SLslaaEgrg  nedRcsgssi  rAlGgdwwgl  rlgaaskqrt  elrcvstarp
C. elegans      ddeqdwEApA  agpRlK....  ...rVrsi..  ..........  ..........
yeast           SaykqlEAde  qVkkRKld..  yApGpKyKak  sksnspapis  attqsnngia
yeast homolog   ..........  ..........  ..........  ..........  ..........
RRM3, S. pombe  gLpirnEnkA  pVqmR.....  ...GVKnK..  ..........  ..........
Consensus       sl----ea-a  -v-rrk----  -a-gvk-k--  ----------  ----------
```

FIG. 3C

```
                    901                                              941
Human               slaQprtntl  qsLtKEhklq  nVHpyfkllf  qGinsvwgh. .
C. elegans          ..........  ..........  ..........  ............ .
yeast               amlQrhsrkr  fqLkKEsnsn  qVHslvsdep  rGqdtedhil  e
yeast homolog       ..........  ..........  ..........  ............ .
RRM3, S. pombe      ..........  ..........  ..........  ............ .
Consensus           ---q------  --l-ke----  -vh-------  -g--------  -
```

FIG. 3D

SEQUENCE LISTING

<160> NUMBER OF SEQ ID NOS: 7

<210> SEQ ID NO 1
<211> LENGTH: 2130
<212> TYPE: DNA
<213> ORGANISM: HUMAN

-continued

```
<400> SEQUENCE: 1
atgctctcgg gcatagaggc ggcggcaggg gaatatgagg actcggagct gcggtgccgc        60
gtggctgtgg aggagctgag cccgggcggg cagccgcgaa ggcgccaggc cctgcgcacc       120
gcggagctga gcctgggtcg caacgagcgc cgcgagttga tgctgcggct gcaagcgcca       180
gggcccgcgg ggcggccgcg ctgcttccct ctgcgcgccg cgcgcctctt cacgcgtttc       240
gccgaggccg ggcgcagcac cctgcggctc cccgcccacg acaccccggg gccggcgca        300
gtgcagctgc tgctctcgga ctgccccca gaccgcctgc gccgcttcct gcgcacattg        360
cgcctcaagc tggctgcggc cccgggtccc gggccggcct ccgcccgagc gcagctgctg       420
ggcccgcggc ccgcgacttt cgtcaccatc agccctgtgc agcccgagga gcggcggctc       480
agggcggcca cccgggttcc ggacactacg ctggtgaagc ggcctgtgga gccccaggct       540
ggggccgagc ctagcacaga agccccaagg tggcccctgc ctgtgaagag gctgagcttg       600
ccctccacca agccacagct ttctgaggaa caggctgctg tgctgagggc cgtcctgaaa       660
ggccagagca tcttcttcac tgggagtgca ggcactgtgg ccactgccag cactggggtg       720
gcagcctgcc acatcggggg caccaccctc catgcctttg caggcatcgg ctcaggccag       780
gctcctctag cccagtgtgt ggccctggcc caaaggccag gcgtgcggca gggctggctg       840
aactgccagc ggttggtcat tgacgagatc tcaatggtga aggcagacct gtttgacaaa       900
ctggaggccg tggccagagc tgtccggcag cagaacaagc cattcggagg gatccagctc       960
atcatctgtg gggactttct gcagctgcca cctgtgacca gggctcccca gccccacgg       1020
ttctgcttcc agtccaagag ctggaagagg tgtgtgccag tgaccctgga gctgaccaag       1080
gtgtggaggc aggcagacca gaccttcatc tctctactgc aggccgtgag ctaggcagg       1140
tgttcagatg aggtgacccg ccagctccag gccacagctt cccacaaggt ggggcgagat      1200
gggattgtgg ccacgaggct ctgcacccac caggatgatg tggccctcac caacgagagg      1260
cggcttcagg agctgccagg taaggtacac agatttgagg ctatggacag caaccctgag      1320
ctggccagta ccctggatgc ccagtgtcct gttagccagc tccttcaact aaagctgggg      1380
gcccaggtga tgctggtgaa aaacttatcg gtgtctcggg gcctggtgaa tggtgcccga      1440
ggggtggtag ttgggttcga ggcagaaggg agagggctac cccaggtgcg gttcctgtgt      1500
ggagtcactg aggtcatcca cgctgaccgc tggacggtgc aggccaccgg gggccagctc      1560
ctcagtcggc agcagctgcc cctccagctg gcctgggcga tgtccatcca agagccaa       1620
ggcatgaccc tggattgtgt ggagatttct ctgggccgtg tgtttgccag tggccaggcc      1680
tatgtggccc tttctcggc ccgcagcctg cagggcctac gtgtgctgga ctttgacccc      1740
atggcggttc gctgtgaccc ccgtgtgctg cacttctatg ccaccctgcg gcggggcagg      1800
agcctcagtc tggctgcaga agggagaggc aatgaagaca ggtgctccgg aagcagcatc      1860
agggctcttg gaggggactg gtggggactc aggctgggtg cagcctccaa acagagaacg      1920
gaacttaggt gtgtctctac agctaggccc agcctagccc agcccagaac aaacaccctt      1980
cagagcctaa ccaaagaaca taagctgcaa aatgtgcacc catattttaa gctgcttttt      2040
caggggataa atagtgtttg gggacattga aatggatgtt ctcaggttgt atttatttcg      2100
gacaaataaa ctagagaatt gtgtaaaaaa                                        2130
```

<210> SEQ ID NO 2
<211> LENGTH: 689
<212> TYPE: PRT
<213> ORGANISM: HUMAN

<400> SEQUENCE: 2

```
Met Leu Ser Gly Ile Glu Ala Ala Gly Glu Tyr Glu Asp Ser Glu
 1               5                  10                  15

Leu Arg Cys Arg Val Ala Val Glu Glu Leu Ser Pro Gly Gly Gln Pro
            20                  25                  30

Arg Arg Arg Gln Ala Leu Arg Thr Ala Glu Leu Ser Leu Gly Arg Asn
        35                  40                  45

Glu Arg Arg Glu Leu Met Leu Arg Leu Gln Ala Pro Gly Pro Ala Gly
    50                  55                  60

Arg Pro Arg Cys Phe Pro Leu Arg Ala Ala Arg Leu Phe Thr Arg Phe
65                  70                  75                  80

Ala Glu Ala Gly Arg Ser Thr Leu Arg Leu Pro Ala His Asp Thr Pro
                85                  90                  95

Gly Ala Gly Ala Val Gln Leu Leu Ser Asp Cys Pro Pro Asp Arg
            100                 105                 110

Leu Arg Arg Phe Leu Arg Thr Leu Arg Leu Lys Leu Ala Ala Pro
        115                 120                 125

Gly Pro Gly Pro Ala Ser Ala Arg Ala Gln Leu Leu Gly Pro Arg Pro
    130                 135                 140

Arg Asp Phe Val Thr Ile Ser Pro Val Gln Pro Glu Glu Arg Arg Leu
145                 150                 155                 160

Arg Ala Ala Thr Arg Val Pro Asp Thr Thr Leu Val Lys Arg Pro Val
                165                 170                 175

Glu Pro Gln Ala Gly Ala Glu Pro Ser Thr Glu Ala Pro Arg Trp Pro
            180                 185                 190

Leu Pro Val Lys Arg Leu Ser Leu Pro Ser Thr Lys Pro Gln Leu Ser
        195                 200                 205

Glu Glu Gln Ala Ala Val Leu Arg Ala Val Leu Lys Gly Gln Ser Ile
    210                 215                 220

Phe Phe Thr Gly Ser Ala Gly Thr Val Ala Thr Ala Ser Thr Gly Val
225                 230                 235                 240

Ala Ala Cys His Ile Gly Gly Thr Thr Leu His Ala Phe Ala Gly Ile
                245                 250                 255

Gly Ser Gly Gln Ala Pro Leu Ala Gln Cys Val Ala Leu Ala Gln Arg
            260                 265                 270

Pro Gly Val Arg Gln Gly Trp Leu Asn Cys Gln Arg Leu Val Ile Asp
        275                 280                 285

Glu Ile Ser Met Val Glu Ala Asp Leu Phe Asp Lys Leu Glu Ala Val
    290                 295                 300

Ala Arg Ala Val Arg Gln Gln Asn Lys Pro Phe Gly Gly Ile Gln Leu
305                 310                 315                 320

Ile Ile Cys Gly Asp Phe Leu Gln Leu Pro Pro Val Thr Lys Gly Ser
                325                 330                 335

Gln Pro Pro Arg Phe Cys Phe Gln Ser Lys Ser Trp Lys Arg Cys Val
            340                 345                 350

Pro Val Thr Leu Glu Leu Thr Lys Val Trp Arg Gln Ala Asp Gln Thr
        355                 360                 365

Phe Ile Ser Leu Leu Gln Ala Val Arg Leu Gly Arg Cys Ser Asp Glu
    370                 375                 380

Val Thr Arg Gln Leu Gln Ala Thr Ala Ser His Lys Val Gly Arg Asp
385                 390                 395                 400

Gly Ile Val Ala Thr Arg Leu Cys Thr His Gln Asp Asp Val Ala Leu
```

-continued

```
                    405                 410                 415
Thr Asn Glu Arg Arg Leu Gln Glu Leu Pro Gly Lys Val His Arg Phe
                420                 425                 430
Glu Ala Met Asp Ser Asn Pro Glu Leu Ala Ser Thr Leu Asp Ala Gln
            435                 440                 445
Cys Pro Val Ser Gln Leu Leu Gln Leu Lys Leu Gly Ala Gln Val Met
        450                 455                 460
Leu Val Lys Asn Leu Ser Val Ser Arg Gly Leu Val Asn Gly Ala Arg
465                 470                 475                 480
Gly Val Val Gly Phe Glu Ala Glu Arg Gly Leu Pro Gln Val
                485                 490                 495
Arg Phe Leu Cys Gly Val Thr Glu Val Ile His Ala Asp Arg Trp Thr
                500                 505                 510
Val Gln Ala Thr Gly Gly Gln Leu Leu Ser Arg Gln Gln Leu Pro Leu
            515                 520                 525
Gln Leu Ala Trp Ala Met Ser Ile His Lys Ser Gln Gly Met Thr Leu
        530                 535                 540
Asp Cys Val Glu Ile Ser Leu Gly Arg Val Phe Ala Ser Gly Gln Ala
545                 550                 555                 560
Tyr Val Ala Leu Ser Arg Ala Arg Ser Leu Gln Gly Leu Arg Val Leu
                565                 570                 575
Asp Phe Asp Pro Met Ala Val Arg Cys Asp Pro Arg Val Leu His Phe
                580                 585                 590
Tyr Ala Thr Leu Arg Arg Gly Arg Ser Leu Ser Leu Ala Ala Glu Gly
            595                 600                 605
Arg Gly Asn Glu Asp Arg Cys Ser Gly Ser Ser Ile Arg Ala Leu Gly
        610                 615                 620
Gly Asp Trp Trp Gly Leu Arg Leu Gly Ala Ala Ser Lys Gln Arg Thr
625                 630                 635                 640
Glu Leu Arg Cys Val Ser Thr Ala Arg Pro Ser Leu Ala Gln Pro Arg
                645                 650                 655
Thr Asn Thr Leu Gln Ser Leu Thr Lys Glu His Lys Leu Gln Asn Val
                660                 665                 670
His Pro Tyr Phe Lys Leu Leu Phe Gln Gly Ile Asn Ser Val Trp Gly
            675                 680                 685
His
```

<210> SEQ ID NO 3
<211> LENGTH: 677
<212> TYPE: PRT
<213> ORGANISM: Caenorhabditis elegans

<400> SEQUENCE: 3

```
Met Ser Lys Ser Leu Gln Thr Asp Glu Asn Gly Gly Val Ser Glu Ser
 1               5                  10                  15
Pro Ser Asn Cys Thr Tyr Cys Tyr Thr Leu Glu Cys Ser Leu Arg Ile
                20                  25                  30
Glu Ser Thr Ser Ser Ile Lys Lys Lys Thr Pro Ile Ser Ser Lys Ser
            35                  40                  45
Ala Ile Met Thr Val Gly Arg Asn Ala Gln Arg Lys Ile His Leu Gln
        50                  55                  60
Ile Glu Leu Lys Thr Thr Ala Thr Gly Gln Pro Ala Val Val Cys Tyr
65                  70                  75                  80
Asp Val Thr Asp Ala Val Val His Leu Gln Ser Val Ala Asn Gly Lys
```

```
                    85                  90                  95
Cys Thr Val Glu Ile Pro Ser Leu Ser Leu Met Phe Gln Met Phe Asn
                100                 105                 110
Cys Ala Pro Arg Lys Leu Asn Val Phe Met Lys Ser Leu Gln Ala Lys
            115                 120                 125
Leu Asp Ile Met Lys Met Glu Lys Ser Pro Ile Ser Ala Val Pro Arg
130                 135                 140
Gln Phe Ser Arg Pro Pro Ala Val Phe Ser Val Leu Ser Pro Leu Thr
145                 150                 155                 160
Ile Ser Glu Met Arg Lys Val Lys Lys Leu Arg Glu Pro Ser Ala Leu
                165                 170                 175
Ala Arg Pro Ser Lys Glu Ala Thr Thr Pro Lys Arg Arg Thr Ser Ser
            180                 185                 190
Met Asn Leu Leu Ala Gly Gly Leu Glu Asn Arg Ile Met Asn Arg Ser
            195                 200                 205
Ile Gly Leu Lys Arg Thr Thr Ser Phe Ala Arg Asp Asp Arg Glu Lys
        210                 215                 220
Ala Glu Thr Leu Val Ser Leu Lys Ser Phe Lys Asp Ala Pro Ala Ile
225                 230                 235                 240
Ser Glu Arg Ile Gln Leu Ser Asp Glu Gln Lys Ser Val Val Arg Cys
                245                 250                 255
Val Ile Asn Ser Arg Thr Ser Val Phe Phe Thr Gly Ser Ala Gly Thr
            260                 265                 270
Gly Lys Ser Val Ile Leu Arg Arg Ile Ile Glu Met Leu Pro Ala Gly
            275                 280                 285
Asn Thr Tyr Ile Thr Ala Ala Thr Gly Val Ala Ala Ser Gln Ile Gly
        290                 295                 300
Gly Ile Thr Leu His Ala Phe Cys Gly Phe Arg Tyr Glu Asn Ser Thr
305                 310                 315                 320
Pro Glu Gln Cys Leu Lys Gln Val Leu Arg Gln Asn His Met Val Arg
                325                 330                 335
Gln Trp Lys Gln Cys Ser His Leu Ile Ile Asp Glu Ile Ser Met Ile
            340                 345                 350
Asp Arg Asp Phe Phe Glu Ala Leu Glu Tyr Val Ala Arg Thr Val Arg
            355                 360                 365
Asn Asn Asp Lys Pro Phe Gly Gly Ile Gln Leu Ile Ile Thr Gly Asp
        370                 375                 380
Phe Phe Gln Leu Pro Pro Val Ser Lys Asp Glu Pro Val Phe Cys Phe
385                 390                 395                 400
Glu Ser Glu Ala Trp Ser Arg Cys Ile Gln Lys Thr Ile Val Leu Lys
                405                 410                 415
Asn Val Lys Arg Gln Asn Asp Asn Val Phe Val Lys Ile Leu Asn Asn
            420                 425                 430
Val Arg Val Gly Lys Cys Asp Phe Lys Ser Ala Asp Ile Leu Lys Glu
            435                 440                 445
Ser Ser Lys Asn Gln Phe Pro Ser Ser Val Ile Pro Thr Lys Leu Cys
        450                 455                 460
Thr His Ser Asp Asp Ala Asp Arg Ile Asn Ser Ser Ile Glu Thr
465                 470                 475                 480
Thr Gln Gly Asp Ala Lys Thr Phe His Ala Tyr Asp Asp Glu Ser Phe
                485                 490                 495
Asp Thr His Ala Lys Ala Arg Thr Leu Ala Gln Lys Lys Leu Val Leu
            500                 505                 510
```

Lys Val Gly Ala Gln Val Met Leu Ile Lys Asn Ile Asp Val Ile Lys
            515                 520                 525

Gly Leu Cys Asn Gly Ser Arg Gly Phe Val Glu Lys Phe Ser Glu Asn
            530                 535                 540

Gly Asn Pro Met Ile Arg Phe Val Ser Gln Ala Asp Ala Ser Ile Glu
545                 550                 555                 560

Ile Arg Arg Ser Lys Phe Ser Val Arg Ile Pro Gly Ser Asp Ala Pro
                565                 570                 575

Leu Ile Arg Arg Gln Leu Pro Leu Gln Leu Ala Trp Ala Ile Ser Ile
            580                 585                 590

His Lys Ser Gln Gly Met Thr Leu Asp Cys Ala Glu Ile Ser Leu Glu
            595                 600                 605

Arg Val Phe Ala Asp Gly Gln Ala Tyr Val Ala Leu Ser Arg Ala Arg
            610                 615                 620

Ser Leu Ala Ala Ile Arg Ile Ile Gly Phe Asp Ala Ser Cys Val Arg
625                 630                 635                 640

Ala Asn Ser Lys Val Ile Asp Phe Tyr Lys Ser Ile Glu Ala Glu Cys
                645                 650                 655

Asp Asp Glu Gln Asp Trp Glu Ala Pro Ala Ala Gly Pro Arg Leu Lys
            660                 665                 670

Arg Val Arg Ser Ile
            675

<210> SEQ ID NO 4
<211> LENGTH: 857
<212> TYPE: PRT
<213> ORGANISM: Saccharomyces cerevisiae

<400> SEQUENCE: 4

Met Pro Lys Trp Ile Arg Ser Thr Leu Asn His Ile Ile Pro Arg Arg
  1               5                  10                  15

Pro Phe Ile Cys Ser Phe Asn Ser Phe Leu Leu Lys Asn Val Ser
                 20                  25                  30

His Ala Lys Leu Ser Phe Ser Met Ser Ser Arg Gly Phe Arg Ser Asn
             35                  40                  45

Asn Phe Ile Gln Ala Gln Leu Lys His Pro Ser Ile Leu Ser Lys Glu
         50                  55                  60

Asp Leu Asp Leu Leu Ser Asp Ser Asp Trp Glu Glu Pro Asp Cys
 65                  70                  75                  80

Ile Gln Leu Glu Thr Glu Lys Gln Glu Lys Lys Ile Ile Thr Asp Ile
                 85                  90                  95

His Lys Glu Asp Pro Val Asp Lys Lys Pro Met Arg Asp Lys Asn Val
            100                 105                 110

Met Asn Phe Ile Asn Lys Asp Ser Pro Leu Ser Trp Asn Asp Met Phe
        115                 120                 125

Lys Pro Ser Ile Ile Gln Pro Pro Gln Leu Ile Ser Glu Asn Ser Phe
    130                 135                 140

Asp Gln Ser Ser Gln Lys Lys Ser Arg Ser Thr Gly Phe Lys Asn Pro
145                 150                 155                 160

Leu Arg Pro Ala Leu Lys Lys Glu Ser Ser Phe Asp Glu Leu Gln Asn
                165                 170                 175

Asn Ser Ile Ser Gln Glu Arg Ser Leu Glu Met Ile Asn Glu Asn Glu
            180                 185                 190

Lys Lys Lys Met Gln Phe Gly Glu Lys Ile Ala Val Leu Thr Gln Arg

-continued

```
            195                 200                 205
Pro Ser Phe Thr Glu Leu Gln Asn Asp Gln Asp Ser Asn Leu Asn
        210                 215                 220

Pro His Asn Gly Val Lys Val Lys Ile Pro Ile Cys Leu Ser Lys Glu
225                 230                 235                 240

Gln Glu Ser Ile Ile Lys Leu Ala Glu Asn Gly His Asn Ile Phe Tyr
                245                 250                 255

Thr Gly Ser Ala Gly Thr Gly Lys Ser Ile Leu Leu Arg Glu Met Ile
                260                 265                 270

Lys Val Leu Lys Gly Ile Tyr Gly Arg Glu Asn Val Ala Val Thr Ala
                275                 280                 285

Ser Thr Gly Leu Ala Ala Cys Asn Ile Gly Gly Ile Thr Ile His Ser
        290                 295                 300

Phe Ala Gly Ile Leu Gly Lys Gly Asp Ala Asp Lys Leu Tyr Lys Lys
305                 310                 315                 320

Val Gly Arg Arg Ser Arg Lys His Leu Arg Arg Trp Glu Asn Ile Gly
                325                 330                 335

Ala Leu Val Val Asp Glu Ile Ser Met Leu Asp Ala Glu Leu Leu Asp
        340                 345                 350

Lys Leu Asp Phe Ile Ala Arg Lys Ile Arg Lys Asn His Gln Pro Phe
        355                 360                 365

Gly Gly Ile Gln Leu Ile Phe Cys Gly Asp Phe Phe Gln Leu Pro Pro
370                 375                 380

Val Ser Lys Asp Pro Asn Arg Pro Thr Lys Phe Ala Phe Glu Ser Lys
385                 390                 395                 400

Ala Trp Lys Glu Gly Val Lys Met Thr Ile Met Leu Gln Lys Val Phe
                405                 410                 415

Arg Gln Arg Gly Asp Val Lys Phe Ile Glu Met Leu Asn Arg Met Arg
                420                 425                 430

Leu Gly Asn Ile Asp Asp Glu Thr Glu Arg Glu Phe Lys Lys Leu Ser
        435                 440                 445

Arg Pro Leu Pro Asp Asp Glu Ile Ile Pro Ala Glu Leu Tyr Ser Thr
450                 455                 460

Arg Met Glu Val Glu Arg Ala Asn Asn Ser Arg Leu Ser Lys Leu Pro
465                 470                 475                 480

Gly Gln Val His Ile Phe Asn Ala Ile Asp Gly Gly Ala Leu Glu Asp
                485                 490                 495

Glu Glu Leu Lys Glu Arg Leu Leu Gln Asn Phe Leu Ala Pro Lys Glu
                500                 505                 510

Leu His Leu Lys Val Gly Ala Gln Val Met Met Val Lys Asn Leu Asp
        515                 520                 525

Ala Thr Leu Val Asn Gly Ser Leu Gly Lys Val Ile Glu Phe Met Asp
530                 535                 540

Pro Glu Thr Tyr Phe Cys Tyr Glu Ala Leu Thr Asn Asp Pro Ser Met
545                 550                 555                 560

Pro Pro Glu Lys Leu Glu Thr Trp Ala Glu Asn Pro Ser Lys Leu Lys
                565                 570                 575

Ala Ala Met Glu Arg Glu Gln Ser Asp Gly Glu Glu Ser Ala Val Ala
                580                 585                 590

Ser Arg Lys Ser Ser Val Lys Glu Gly Phe Ala Lys Ser Asp Ile Gly
        595                 600                 605

Glu Pro Val Ser Pro Leu Asp Ser Ser Val Phe Asp Phe Met Lys Arg
610                 615                 620
```

```
Val Lys Thr Asp Asp Glu Val Val Leu Glu Asn Ile Lys Arg Lys Glu
625                 630                 635                 640

Gln Leu Met Gln Thr Ile His Gln Asn Ser Ala Gly Lys Arg Arg Leu
            645                 650                 655

Pro Leu Val Arg Phe Lys Ala Ser Asp Met Ser Thr Arg Met Val Leu
            660                 665                 670

Val Glu Pro Glu Asp Trp Ala Ile Glu Asp Glu Asn Glu Lys Pro Leu
        675                 680                 685

Val Ser Arg Val Gln Leu Pro Leu Met Leu Ala Trp Ser Leu Ser Ile
    690                 695                 700

His Lys Ser Gln Gly Gln Thr Leu Pro Lys Val Lys Val Asp Leu Arg
705                 710                 715                 720

Arg Val Phe Glu Lys Gly Gln Ala Tyr Val Ala Leu Ser Arg Ala Val
                725                 730                 735

Ser Arg Glu Gly Leu Gln Val Leu Asn Phe Asp Arg Thr Arg Ile Lys
            740                 745                 750

Ala His Gln Lys Val Ile Asp Phe Tyr Leu Thr Leu Ser Ser Ala Glu
            755                 760                 765

Ser Ala Tyr Lys Gln Leu Glu Ala Asp Glu Gln Val Lys Lys Arg Lys
770                 775                 780

Leu Asp Tyr Ala Pro Gly Pro Lys Tyr Lys Ala Lys Ser Lys Ser Asn
785                 790                 795                 800

Ser Pro Ala Pro Ile Ser Ala Thr Thr Gln Ser Asn Asn Gly Ile Ala
                805                 810                 815

Ala Met Leu Gln Arg His Ser Arg Lys Arg Phe Gln Leu Lys Lys Glu
            820                 825                 830

Ser Asn Ser Asn Gln Val His Ser Leu Val Ser Asp Glu Pro Arg Gly
            835                 840                 845

Gln Asp Thr Glu Asp His Ile Leu Glu
    850                 855

<210> SEQ ID NO 5
<211> LENGTH: 723
<212> TYPE: PRT
<213> ORGANISM: yeast homolog

<400> SEQUENCE: 5

Met Phe Arg Ser His Ala Ser Gly Asn Lys Lys Gln Trp Ser Lys Arg
1               5                   10                  15

Ser Ser Asn Gly Ser Thr Pro Ala Ala Ser Ala Ser Gly Ser His Ala
            20                  25                  30

Tyr Arg Gln Gln Thr Leu Ser Ser Phe Phe Met Gly Cys Gly Lys Lys
        35                  40                  45

Ser Ala Ala Ala Ser Lys Asn Ser Thr Thr Ile Ile Asp Leu Glu Ser
    50                  55                  60

Gly Asp Glu Gly Asn Arg Asn Ile Thr Ala Pro Pro Arg Pro Arg Leu
65                  70                  75                  80

Ile Arg Asn Asn Ser Ser Ser Leu Phe Ser Gln Ser Gln Gly Ser Phe
                85                  90                  95

Gly Asp Asp Asp Pro Asp Ala Glu Phe Lys Lys Leu Val Asp Val Pro
            100                 105                 110

Arg Leu Asn Ser Tyr Lys Lys Ser Ser Arg Ser Leu Ser Met Thr Ser
        115                 120                 125

Ser Leu His Lys Thr Ala Ser Ala Ser Thr Thr Gln Lys Thr Tyr His
```

```
            130                 135                 140
Phe Asp Glu Asp Glu Thr Leu Arg Glu Val Thr Ser Val Lys Ser Asn
145                 150                 155                 160

Ser Arg Gln Leu Ser Phe Thr Ser Thr Ile Asn Ile Glu Asp Ser Ser
                165                 170                 175

Met Lys Leu Ser Thr Asp Ser Glu Arg Pro Ala Lys Arg Ser Lys Pro
            180                 185                 190

Ser Met Glu Phe Gln Gly Leu Lys Leu Thr Val Pro Lys Lys Ile Lys
            195                 200                 205

Pro Leu Leu Arg Lys Thr Val Ser Asn Met Asp Ser Met Asn His Arg
210                 215                 220

Ser Ala Ser Ser Pro Val Val Leu Thr Met Glu Gln Glu Arg Val Val
225                 230                 235                 240

Asn Leu Ile Val Lys Lys Arg Thr Asn Val Phe Tyr Thr Gly Ser Ala
                245                 250                 255

Gly Thr Gly Lys Ser Val Ile Leu Gln Thr Ile Ile Arg Gln Leu Ser
                260                 265                 270

Ser Leu Tyr Gly Lys Glu Ser Ile Ala Ile Thr Ala Ser Thr Gly Leu
            275                 280                 285

Ala Ala Val Thr Ile Gly Gly Ser Thr Leu His Lys Trp Ser Gly Ile
290                 295                 300

Gly Ile Gly Asn Lys Thr Ile Asp Gln Leu Val Lys Lys Ile Gln Ser
305                 310                 315                 320

Gln Lys Asp Leu Leu Ala Ala Trp Arg Tyr Thr Lys Val Leu Ile Ile
                325                 330                 335

Asp Glu Ile Ser Met Val Asp Gly Asn Leu Leu Asp Lys Leu Glu Gln
            340                 345                 350

Ile Ala Arg Arg Ile Arg Lys Asn Asp Asp Pro Phe Gly Gly Ile Gln
            355                 360                 365

Leu Val Leu Thr Gly Asp Phe Phe Gln Leu Pro Pro Val Ala Lys Lys
370                 375                 380

Asp Glu His Asn Val Val Lys Phe Cys Phe Glu Ser Glu Met Trp Lys
385                 390                 395                 400

Arg Cys Ile Gln Lys Thr Ile Leu Leu Thr Lys Val Phe Arg Gln Gln
                405                 410                 415

Asp Asn Lys Leu Ile Asp Ile Leu Asn Ala Ile Arg Tyr Gly Glu Leu
                420                 425                 430

Thr Val Asp Ile Ala Lys Thr Ile Arg Asn Leu Asn Arg Asp Ile Asp
            435                 440                 445

Tyr Ala Asp Gly Ile Ala Pro Thr Glu Leu Tyr Ala Thr Arg Arg Glu
450                 455                 460

Val Glu Leu Ser Asn Val Lys Lys Leu Gln Ser Leu Pro Gly Asp Leu
465                 470                 475                 480

Tyr Glu Phe Lys Ala Val Asp Asn Ala Pro Glu Arg Tyr Gln Ala Ile
                485                 490                 495

Leu Asp Ser Ser Leu Met Val Glu Lys Val Val Ala Leu Lys Glu Asp
            500                 505                 510

Ala Gln Val Met Met Leu Lys Asn Lys Pro Asp Val Glu Leu Val Asn
            515                 520                 525

Gly Ser Leu Gly Lys Val Leu Phe Phe Val Thr Glu Ser Leu Val Val
            530                 535                 540

Lys Met Lys Glu Ile Tyr Lys Ile Val Asp Asp Glu Val Val Met Asp
545                 550                 555                 560
```

```
Met Arg Leu Val Ser Arg Val Ile Gly Asn Pro Leu Lys Glu Ser
                565                 570                 575

Lys Glu Phe Arg Gln Asp Leu Asn Ala Arg Pro Leu Ala Arg Leu Glu
            580                 585                 590

Arg Leu Lys Ile Leu Ile Asn Tyr Ala Val Lys Ile Ser Pro His Lys
        595                 600                 605

Glu Lys Phe Pro Tyr Val Arg Trp Thr Val Gly Lys Asn Lys Tyr Ile
    610                 615                 620

His Glu Leu Met Val Pro Glu Arg Phe Pro Ile Asp Ile Pro Arg Glu
625                 630                 635                 640

Asn Val Gly Leu Glu Arg Thr Gln Ile Pro Leu Met Leu Cys Trp Ala
                645                 650                 655

Leu Ser Ile His Lys Ala Gln Gly Gln Thr Ile Gln Arg Leu Lys Val
                660                 665                 670

Asp Leu Arg Arg Ile Phe Glu Ala Gly Gln Val Tyr Val Ala Leu Ser
                675                 680                 685

Arg Ala Val Thr Met Asp Thr Leu Gln Val Leu Asn Phe Asp Pro Gly
            690                 695                 700

Lys Ile Arg Thr Asn Glu Arg Val Lys Asp Phe Tyr Lys Arg Leu Glu
705                 710                 715                 720

Thr Leu Lys

<210> SEQ ID NO 6
<211> LENGTH: 805
<212> TYPE: PRT
<213> ORGANISM: Schizosaccharomyces pombe

<400> SEQUENCE: 6

Met Phe Ser Cys Gln Ser Leu Tyr Lys Phe Ser His Ser Phe Arg Lys
  1               5                  10                  15

Arg Ile Pro Val Met Phe Gln Arg Ala Gln Gln Lys Ser Ser Leu Leu
             20                  25                  30

His Thr Gln Asn Glu Ser Ser His Gln Pro Ser Leu Asn Lys Leu Gly
         35                  40                  45

Gly Phe Ser Ser Ala Ser Leu Asn Phe Asn Ser Arg Ser Ser Thr
     50                  55                  60

Asn Asp Asp Gln Gln Thr Phe Ser Ser Gln Ser Asp Asn Leu Pro Ser
 65                  70                  75                  80

Ser Pro Ile Thr Leu Pro Ala Lys Arg Gly Arg Ser Ala Ala Ser Leu
                 85                  90                  95

Lys Gln Leu Asp Asn Thr Val Gly Phe Asp Val Ser Lys Pro Ser Leu
            100                 105                 110

Pro Val Phe Glu Asn Ser Gly Leu Gly Ser Lys Tyr Ser Thr Glu Ile
        115                 120                 125

Ala Asn Gly Val Tyr Ile Asp Glu Asn Asp Phe Asp Asp Leu Leu
    130                 135                 140

Leu Glu Asn Asp Ile Asp Gln Lys Pro Ile Pro Trp Ser Ser Ser Pro
145                 150                 155                 160

Ile Glu His Thr Lys Leu Thr Lys Ser Met Leu Ser Ser Glu Lys Arg
                165                 170                 175

Ser Lys Asn His Leu Ser Lys Ile Tyr Glu Asp His Thr Ser Glu Lys
            180                 185                 190

Gly Ala Ser Ser Val Ile Ser Ser Asn Ile Ala Arg Gln Gly Ile Lys
        195                 200                 205
```

-continued

```
Arg Ser Arg Thr Leu Pro Trp Ala Val Asp Pro Tyr Arg Tyr Gly Asp
    210                 215                 220

Pro Asp Pro Lys Arg Thr Ser Thr Ser Ala Asp Ile Ser Gln His Thr
225                 230                 235                 240

Val Ser Asn Asp Ser Ser Asn Lys Leu Ser Asn Gly Arg Ser Ser Ser
                245                 250                 255

Leu Asp Ser Leu Ala Lys Lys Arg Met Ser Lys Ser Lys Ser Thr Pro
            260                 265                 270

Gln Ile Ser Lys Lys Phe Ser Val Pro Leu Asn Ser Ala Ser Lys Ser
        275                 280                 285

Pro Ile Gly Ser Ser Leu Phe Lys Thr Ser Asp Ser Arg Lys Lys Ser
    290                 295                 300

Val Pro Ser Ile Phe Leu Ser Asp Glu Gln Lys Arg Ile Leu Asp Met
305                 310                 315                 320

Val Val Glu Gln Gln His Ser Ile Phe Phe Thr Gly Ser Ala Gly Thr
                325                 330                 335

Gly Lys Ser Val Leu Leu Arg Lys Ile Ile Glu Val Leu Lys Ser Lys
            340                 345                 350

Tyr Arg Lys Gln Ser Asp Arg Val Ala Val Thr Ala Ser Thr Gly Leu
        355                 360                 365

Ala Ala Cys Asn Ile Gly Gly Val Thr Leu His Ser Phe Ala Gly Val
    370                 375                 380

Gly Leu Ala Arg Glu Ser Val Asp Leu Leu Val Ser Lys Ile Lys Lys
385                 390                 395                 400

Asn Lys Lys Cys Val Asn Arg Trp Leu Arg Thr Arg Val Leu Ile Ile
                405                 410                 415

Asp Glu Val Ser Met Val Asp Ala Glu Leu Met Asp Lys Leu Glu Glu
            420                 425                 430

Val Ala Arg Val Ile Arg Lys Asp Ser Lys Pro Phe Gly Gly Ile Gln
        435                 440                 445

Leu Val Leu Thr Gly Asp Phe Phe Gln Leu Pro Pro Val Pro Glu Asn
    450                 455                 460

Gly Lys Glu Ser Lys Phe Cys Phe Glu Ser Gln Thr Trp Lys Ser Ala
465                 470                 475                 480

Leu Asp Phe Thr Ile Gly Leu Thr His Val Phe Arg Gln Lys Asp Glu
                485                 490                 495

Glu Phe Val Lys Met Leu Asn Glu Leu Arg Leu Gly Lys Leu Ser Asp
            500                 505                 510

Glu Ser Val Arg Lys Phe Lys Val Leu Asn Arg Thr Ile Glu Tyr Glu
        515                 520                 525

Asp Gly Leu Leu Pro Thr Glu Leu Phe Pro Thr Arg Tyr Glu Val Glu
    530                 535                 540

Arg Ser Asn Asp Met Arg Met Gln Gln Ile Asn Gln Asn Pro Val Thr
545                 550                 555                 560

Phe Thr Ala Ile Asp Ser Gly Thr Val Arg Asp Lys Glu Phe Arg Asp
                565                 570                 575

Arg Leu Leu Gln Gly Cys Met Ala Pro Ala Thr Leu Val Leu Lys Val
            580                 585                 590

Asn Ala Gln Val Met Leu Ile Lys Asn Ile Asp Asp Gln Leu Val Asn
        595                 600                 605

Gly Ser Leu Gly Lys Val Ile Gly Phe Ile Asp Asp Glu Thr Tyr Gln
    610                 615                 620
```

```
Met Glu Lys Lys Asp Ala Glu Met Gln Gly Arg Asn Ala Phe Glu Tyr
625                 630                 635                 640

Asp Ser Leu Asp Ile Ser Pro Phe Asp Leu Pro Asp Val Lys Gln Lys
                645                 650                 655

Lys Tyr Lys Leu Ile Ala Met Arg Lys Ala Ser Ser Thr Ala Ile Lys
                660                 665                 670

Trp Pro Leu Val Arg Phe Lys Leu Pro Asn Gly Gly Glu Arg Thr Ile
                675                 680                 685

Val Val Gln Arg Glu Thr Trp Asn Ile Glu Leu Pro Asn Gly Glu Val
    690                 695                 700

Gln Ala Ser Arg Ser Gln Ile Pro Leu Ile Leu Ala Tyr Ala Ile Ser
705                 710                 715                 720

Ile His Lys Ala Gln Gly Gln Thr Leu Asp Arg Val Lys Val Asp Leu
                725                 730                 735

Gly Arg Val Phe Glu Lys Gly Gln Ala Tyr Val Ala Leu Ser Arg Ala
                740                 745                 750

Thr Thr Gln Glu Gly Leu Gln Val Leu Asn Phe Ser Pro Ala Lys Val
                755                 760                 765

Met Ala His Pro Lys Val Val Gln Phe Tyr Lys Gln Leu Ala Ser Val
    770                 775                 780

Asn Gly Leu Pro Ile Arg Asn Glu Asn Lys Ala Pro Val Gln Met Arg
785                 790                 795                 800

Gly Val Lys Asn Lys
                805

<210> SEQ ID NO 7
<211> LENGTH: 556
<212> TYPE: PRT
<213> ORGANISM: Artificial Sequence
<220> FEATURE:
<223> OTHER INFORMATION: Description of Artificial Sequence:consensus
      sequence

<400> SEQUENCE: 7

Pro Met Phe Arg Ser His Ser Gly Asn Ser Arg Pro Ser Asn Cys Ser
  1               5                  10                  15

Leu Asn Ala Ser Ser Ser Gln Gln Phe Ser Ser Gln Ser Gly Ser Ala
                 20                  25                  30

Ile Ala Gly Asn Arg Ile Ser Leu Glu Leu Asp Thr Gly Pro Cys Pro
             35                  40                  45

Leu Glu Leu Ser Lys Phe Ser Thr Glu Ile Ala Asn Gly Asp Glu Asp
         50                  55                  60

Pro Asp Leu Lys Asn Leu Met Asp Cys Ile Pro Arg Ser Pro Leu Ser
 65                  70                  75                  80

Phe Lys Ser Arg Ser Ile Leu His Lys Ser Ala Ser Ser Ala Ser Gln
                 85                  90                  95

Gln Ser Arg Lys Arg Ser Arg Thr Leu Pro Thr Ser Pro Val Arg Leu
                100                 105                 110

Glu Ser Ser Ala Ile Asn Thr Asp Ser Lys Ser Asn Ser Leu Ala Lys
            115                 120                 125

Arg Ser Lys Ser Ile Lys Lys Thr Thr Val Pro Ser Ala Pro Pro Thr
        130                 135                 140

Val Ser Asn Leu Lys Ser Asn Arg Ala Ser Ser Pro Ile Gln Leu Ser
145                 150                 155                 160

Asp Glu Gln Val Arg Leu Val Val Glu Lys Ser Ile Phe Phe Thr Gly
                165                 170                 175
```

```
Ser Ala Gly Thr Gly Lys Ser Val Leu Arg Ile Ile Glu Val Leu Lys
            180                 185                 190

Ser Tyr Gly Lys Glu Ser Val Ala Thr Ala Ser Thr Gly Leu Ala Ala
            195                 200                 205

Cys Asn Ile Gly Gly Ile Thr Leu His Phe Ala Gly Ile Gly Leu Gly
            210                 215                 220

Asn Thr Asp Gln Leu Val Lys Lys Gln Arg Gln Lys Lys Arg Arg Trp
225                 230                 235                 240

Leu Asn Val Leu Ile Ile Asp Glu Ile Ser Met Val Asp Ala Leu Asp
                245                 250                 255

Lys Leu Glu Val Ala Arg Ile Arg Lys Asn Asp Lys Pro Phe Gly Gly
            260                 265                 270

Ile Gln Leu Ile Thr Gly Asp Phe Phe Gln Leu Pro Pro Val Ser Lys
            275                 280                 285

Asp Glu Pro Pro Lys Phe Cys Phe Glu Ser Ala Trp Lys Arg Cys Gln
            290                 295                 300

Lys Thr Ile Leu Thr Lys Val Phe Arg Gln Asp Asn Lys Phe Ile Lys
305                 310                 315                 320

Leu Asn Ala Val Arg Leu Gly Lys Asp Glu Ser Ala Arg Lys Leu Arg
            325                 330                 335

Ile Tyr Asp Gly Ile Ile Pro Thr Glu Leu Thr Thr Arg Asp Glu Val
            340                 345                 350

Glu Arg Ser Asn Ser Arg Leu Gln Leu Pro Gly Asp Val His Phe Ala
            355                 360                 365

Ile Asp Ser Gly Pro Glu Arg Asp Glu Leu Arg Leu Cys Ala Pro Lys
            370                 375                 380

Leu Val Leu Lys Val Gly Ala Gln Val Met Leu Lys Asn Asp Leu Val
385                 390                 395                 400

Asn Gly Ser Leu Gly Lys Val Gly Phe Val Asp Glu Thr Tyr Lys Ala
            405                 410                 415

Met Arg Ser Arg Asn Phe Glu Lys Glu Leu Asp Ser Phe Asp Leu Lys
            420                 425                 430

Arg Lys Lys Leu Lys Ser Lys Arg Lys Leu Pro Leu Val Arg Phe Lys
            435                 440                 445

Gly Asn Arg Thr Ile Val Val Arg Glu Arg Trp Ile Glu Ile Pro Val
            450                 455                 460

Leu Leu Ser Arg Gln Leu Pro Leu Leu Ala Trp Ala Ser Ile His Lys
465                 470                 475                 480

Ser Gln Gly Gln Thr Leu Asp Val Lys Val Asp Leu Arg Val Phe Glu
            485                 490                 495

Lys Gly Gln Ala Tyr Val Ala Leu Ser Arg Ala Ser Leu Glu Gly Leu
            500                 505                 510

Gln Val Leu Asn Phe Asp Pro Lys Val Arg Ala Pro Lys Val Ile Asp
            515                 520                 525

Phe Tyr Lys Thr Leu Glu Ser Ser Leu Glu Ala Ala Val Arg Arg Lys
            530                 535                 540

Ala Gly Val Lys Lys Gln Leu Lys Glu Val His Gly
545                 550                 555
```

HUMAN HOMOLOGUE OF YEAST HELICASE AND USES THEREOF

FIELD OF THE INVENTION

The present invention describes the nucleotide sequence of the human homologue of a yeast helicase, pif1, the amino acid sequence of the protein, and uses of the helicase. Preferably, the invention comprises a human Pif-1 type helicase.

BACKGROUND OF THE INVENTION

Normal human somatic cells (e.g., fibroblasts, endothelial, and epithelial cells) display a finite replicative capacity of 50–100 population doublings characterized by a cessation of proliferation in spite of the presence of abundant growth factors. This cessation of replication in vitro is variously referred to as cellular senescence or cellular aging. The replicative life span of cells is inversely proportional to the in vivo age of the donor, therefore, cellular senescence is suggested to play an important role in aging in vivo.

Cellular immortalization (the acquisition of unlimited replicative capacity) may be thought of as an abnormal escape from cellular senescence. Shay et al., Exp. Cell Res. (1991) 196:33. Normal human somatic cells appear to be mortal, i.e., have finite replicative potential. In contrast, the germ line and malignant tumor cells are immortal (have indefinite proliferative potential). Human cells cultured in vitro appear to require the aid of transforming viral oncoproteins and telomerase overexpression to become immortal (Hahn et al., Nature 400:464–468,1999).

DNA at chromosome ends is maintained in a dynamic balance of loss and addition of telomeric simple sequence repeats. Sequence loss occurs during cell replication, in part from incomplete replication of chromosome termini by DNA-dependent DNA polymerase. Telomeric repeat addition is catalyzed by the enzyme telomerase: a ribonucleoprotein enzyme which uses a short region within the RNA as a template for the polymerase reaction. Although cells can maintain a constant number of telomeric repeats by balancing loss and addition, not all cells do so. Human germline and cancer cells maintain a constant number of telomeric repeats, while normal human somatic cells lose telomeric repeats with each cycle of cell division. As described above, cells that do not maintain stable telomere length demonstrate a limited proliferative capacity; these cells senesce after a number of population doublings correlated with the erosion of telomeres to a critical minimum length.

Because normal somatic cells do not appear to express or require telomerase and do not maintain chromosome ends, and because all or almost all cancer cells express high levels of telomerase activity and maintain chromosome ends, molecules that inhibit or alter telomerase activity could provide effective and non-toxic anti-cancer agents. Similarly, inhibition of telomerase in parasitic or infectious agents (e.g., trypanosomes, fungi, etc.) could provide a specific approach for reducing the viability or proliferation of these agents. Conversely, activation of telomerase in proliferation-restricted cells (such as normal somatic cells, e.g., of the blood, vasculature, liver, skin, etc.) could provide a mechanism for promoting additional proliferative lifespan (i.e., avoid cellular senescence, Hahn et al, 1999). For a review of telomerase and its function, see U.S. Pat. No. 5,770,422 incorporated herein by reference in its entirety.

Pif-1 helicase has been identified in the yeast Saccharomyces as a required participant of both de novo telomere formation and telomere elongation. U.S. Pat. No. 5,466,576 (incorporated by reference herein in its entirety). Pif-1 helicase works by controlling the activity of telomerase and/or interaction with components of the replication machinery. Deletion mutations of either yeast pif1 or its closely related antagonic pif-like helicase RRM3 affects the ability of the cells to replicate and to maintain their normal telomere length(i.e., helicase is related to cell senescence). The recent discovery of loop structures at telomeric DNA ends suggests an important role for helicases in telomere maintenance and replication (Griffith et al., Cell97:503–514, 1999)

A need exists in the art to know the nucleic acid sequence of human pif-1 helicase, in order to effectively screen for [small molecules] targets which modulate helicase activity. Such compounds that modulate helicase activity are useful in two ways: (1) By decreasing the activity of human helicase, the level of telomerase activity or the size of telomeres will be reduced and the viability of the cell is reduced (i.e., replication delayed, slowed down or arrested); and (2) by increasing the helicase activity within a cell, the activity of the telomerase or the length of telomeres may be increased and the viability of the cell increased (i.e., avoid cellular senescence). Applicants, therefore, provide herein for the first time the nucleic acid and amino acid sequence of human Pif-1 type helicase, the only mammalian helicase involved in telomere maintenance described up to now.

SUMMARY OF THE INVENTION

Applicants provide herein the nucleic acid sequence of human Pif-1 helicase. Also provided in the amino acid sequence of human Pif-1 helicase, as well as methods for screening for compounds that are capable of modulating the activity of human helicase. Thus, the present invention therefore provides a purified and isolated nucleic acid molecule, preferably a DNA molecule, having a sequence which codes for a human helicase, or an oligonucleotide fragment of the nucleic acid molecule which is unique to the human Pif-1 helicase of the invention and include host cells and expression vectors useful in the expression of human Pif-1 helicase. In a preferred embodiment of the invention, the purified and isolated nucleic acid molecule has the sequence as shown in SEQ ID NO:1.

The invention also contemplates a double stranded nucleic acid molecule comprising a nucleic acid molecule of the invention or an oligonucleotide fragment thereof hydrogen bonded to a complementary nucleotide base sequence.

The present invention also provides: (a) a purified and isolated nucleic acid molecule comprising a sequence as shown in SEQ ID NO:1; (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions. In particular, those sequences containing conserved motifs characteristic of helicases.

The present invention also relates to methods of affecting the viability of a cell or cells by contacting the cell or cells with a modulator of the activity of human Pif-1 helicase in the cell. Such contacting specifically increases or decreases the activity of the helicase in that cell or cells, and therefore the viability of the cell or cells. Preferably such modulators are specific inhibitors of human Pif-1 helicase. Preferably, such modulators are small chemically defined molecules or other polypeptides affecting the helicase activity.

Other features and advantages of the invention will be apparent from the following description of the preferred embodiments thereof, and from the claims. All references cited herein, whether supra or infra, are hereby incorporated by reference in their entirety.

DESCRIPTION OF THE FIGURES

FIG. 1

Figure 4:
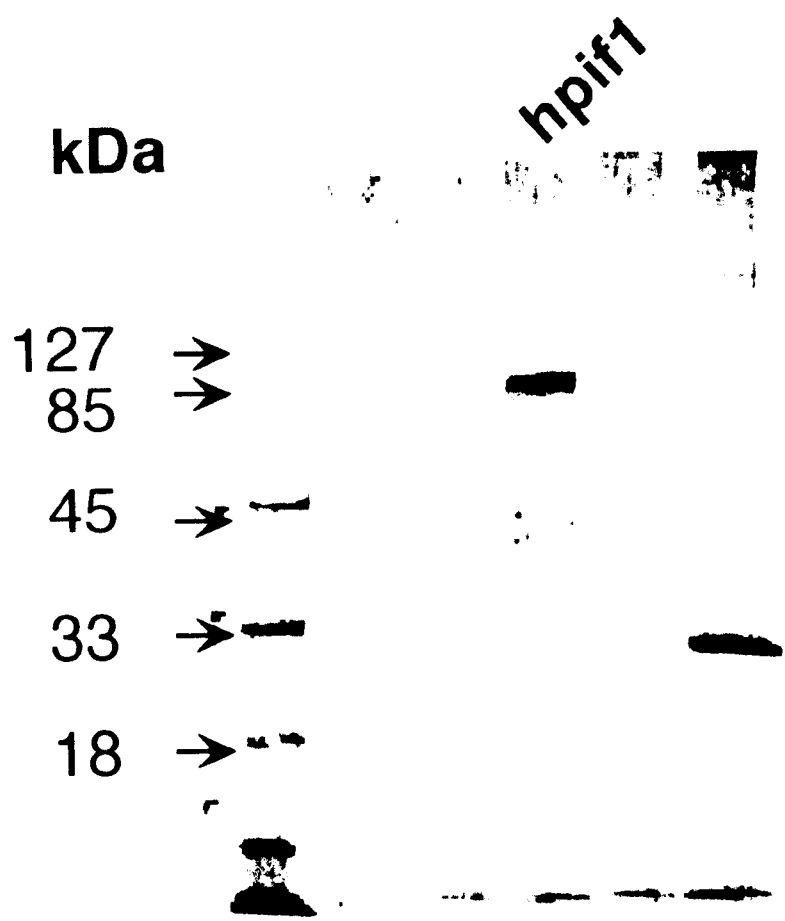

Sequence of the isolated nucleic acid molecule, (SEQ ID NO:1.).

FIG. 2

Predicted human pif1 coding region, (SEQ ID NO:2.). The predicted amino acid sequence is shown below the nucleotide sequence in lower-case letters. The region of the nucleotide sequence that overlaps STS SHGC-13832 (GenBank Accession number G14858, deposited by Richard Myers, Stanford Human Genome Center) is shown in bold-face characters.

FIG. 3

Comparison of predicted protein sequence with pif1 homologs. In the following figure, residues matching to the consensus sequence are shown in upper-case letters. The consensus sequence (SEQ ID NO:7) contains residues that match in 50% or more of the sequences. The consensus sequence is shown in upper case when the amino acid is conserved in all sequences. The sequences shown include *Caenorhabditis elegans* PIF1 (GenBank accession number ABO 15041, deposited by T. Matsuda, Osaka University), (SEQ ID NO:3) yeast (*Saccharomyces cerevisiae*) PIF1 (PIR entry A29457, F. Foury and A. Lahaye, *EMBO J*. 6, 1441 –1449, 1987) (SEQ. ID NO:4) and PIF1 homolog YHR031c (PIR entry S46744, GenBank accession number U00062, M. Johnson, *Science* 265, 2077–2082, 1994) (SEQ ID NO:5), and *Schizosaccharomyces pombe* RRM3/PIF1 homolog rph1 (GenBank accession number AF074944, deposited by V. P. Shultz, and V. A. Zakian., Princeton University) (SEQ ID NO:6). The locations of the binding motifs and putative DNA binding site were taken from PIR entry A29457 for yeast PIF 1.

FIG. 4.

In vitro translation of the human pif1 cDNA in a reticulocyte cell lysate. The cDNA was transcribed by T3 RNA polymerase and translated in the presence of $^{35}$S methionine. The labelled proteins were separated in a 10% polyacrylamide gel as is known in the art. The gel was dryed and an autoradiograph is shown below. The band at approximately 80 kDa corresponds to the hpif1 full length proton predicted from the cDNA sequence.

DETAILED DESCRIPTION OF THE INVENTION

The present invention discloses the nucleic acid sequence encoding human Pif-1 type helicase, preferably comprising the nucleic acid sequence as shown in SEQ ID NO:1. A plasmid containing a nucleic acid sequence encoding human helicase has been deposited with the American Type Culture Collection ("ATCC"), 10801 University Boulevard, Manassas, Va. 20110-2209, and has been given ATCC Accession Number 204169. The deposit referred to herein will be maintained under the terms of the Budapest Treaty on the International Recognition of the Deposit of Micro-Organisms for purposes of Patent Procedure. These deposits are provided merely as convenience to those of skill in the art and are not an admission that a deposit is required under 35 U.S.C. §112. The sequence(s) of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention relates to the nucleic acid sequence or a fragment thereof (referred to herein as a "polynucleotide") of the novel human helicase as shown in FIG. 1 (SEQ ID NO:1), as well as to the amino acid sequence of the human helicase (SEQ ID NO:2), and biologically active portions thereof. By "biologically active portions" is meant portions of the human Pif-1 type helicase of the present invention that exhibit the activity of the helicase (i.e., affect telomere formation or elongation), or are involved in DNA binding, in DNA strand separation, or are involved in ATP binding or hydrolysis by the helicase.

In a preferred embodiment the human Pif-1 type helicase of the present invention is encoded by the nucleic acid sequence shown in Figure SEQ ID NO1.

In a preferred embodiment the human Pif-1 type helicase comprises the amino acid sequence encoded by this nucleic acid sequence. The most probable sequence deduced from these data is shown in Figure SEQ ID NO2.

The present invention further relates to variants of the herein above described nucleic acid sequence which encode for fragments, analogs and derivatives of the polypeptide having the deduced amino acid sequence of SEQ ID NO:2 or the polypeptide encoded by the cDNA of the deposited clone. The variants of the nucleic acid sequence may be naturally occurring variants of the nucleic acid sequence or non-naturally occurring variants of the nucleic acid sequence.

Thus, the present invention includes polynucleotides encoding the same mature polypeptide as shown in SEQ ID NO:2, or the same mature polypeptide encoded by the cDNA of the deposited clone as well as variants of such polynucleotides which variants encode for a fragment, derivative or analog of the polypeptide of SEQ ID NO:2 or the polypeptide encoded by the cDNA of the deposited clone. Such nucleotide variants include deletion variants, substitution variants and addition or insertion variants.

The terms "isolated and purified nucleic acid" and "substantially pure nucleic acid", e.g., substantially pure DNA, refer to a nucleic acid molecule which is one or both of the following: (1) not immediately contiguous with either one or both of the sequences, e.g., coding sequences, with which it is immediately contiguous (i.e., one at the 5'end and one at the 3'end) in the naturally occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure or isolated and purified DNA also includes a recombinant DNA which is part of a hybrid gene encoding additional proteins.

The invention encompasses in one embodiment: (a) an isolated and purified nucleic acid molecule comprising a sequence encoding human helicase protein (the most probable amino acid sequence deduced from these data is shown in SEQ ID NO:2); (b) nucleic acid sequences complementary to (a); (c) nucleic acid sequences which exhibit at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

Given the homologies detected between human and yeast pif1 helicases, similar or higher degrees of homology should exist with more closely related mammalian sequences, like rodent, ape, etc.

The degree of homology (percent identity) between a native and a mutant sequence may be determined, for example, by comparing the two sequences using computer programs commonly employed for this purpose. One suitable program is the GAP computer program described by Devereux et al., (1984) Nucl. Acids Res. 12:387. The GAP program utilizes the alignment method of Needleman and Wunsch (1970) J. Mol. Biol. 48:433, as revised by Smith and Waterman (1981) Adv. Appl. Math. 2:482. Briefly, the GAP program defines identity as the number of aligned symbols (i.e., nucleotides or amino acids) which are identical, divided by the total number of symbols in the shorter of the two sequences.

As used herein the term "stringent conditions" encompasses conditions known in the art under which a nucleotide sequence will hybridize to an isolated and purified nucleic acid molecule comprising a sequence encoding a protein having the amino acid sequence as shown herein, or to (b) a nucleic acid sequence complementary to (a). Screening polynucleotides under stringent conditions may be carried out according to the method described in Nature, 313:402–404 (1985). Polynucleotide sequences capable of hybridizing under stringent conditions with the polynucleotides of the present invention may be, for example, allelic variants of the disclosed DNA sequences, or may be derived from other mammalian sources. General techniques of nucleic acid hybridization are disclosed by Sambrook et al., "Molecular Cloning: A Laboratory Manual", 2nd Ed., Cold Spring Harbor Laboratory, Cold Spring Harbor, N.Y. (1984); and by Haymes et al., "Nucleic Acid Hybridization: A Practical Approach", IRL Press, Washington, D.C. (1985), which references are incorporated herein by reference.

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as hybridization probes for a cDNA library to isolate the full length gene and to isolate other genes which have a high sequence similarity to a gene of the present invention or similar biological activity. Probes of this type preferably have at least between 20 and 30 bases, and may contain, for example, 50 or more bases. The probes may also be used to identify a cDNA clone corresponding to a full length transcript and a genomic clone or clones that contain the complete gene of the present invention including regulatory and promoter regions, exons, and introns.

The present invention further relates to polynucleotides that hybridize to the polynucleotide sequences disclosed herein, if there is at least 80%, preferably at least 90%, more preferably at least 95%, and more preferably at least 98% identity between the sequences. The present invention particularly relates to polynucleotides which hybridize under stringent conditions to the polynucleotides described herein.

Alternatively the polynucleotide may have at least 20 bases, preferably at least 30 bases, and more preferably at least 50 bases which hybridize to a polynucleotide of the present invention and which has an identity thereto, as herein above described, and which may or may not retain activity. For example, such polynucleotides may be employed as probes for the polynucleotide of SEQ ID NO:1, for example for recovery of the polynucleotide or as a diagnostic probe or as a PCR primer.

Thus the present invention is directed to polynucleotides having at least 80% identity, preferably at least 90%, more preferably at least 95%, and more preferably at least 98% identity to a polynucleotide of the present invention, including polynucleotides encoding the polypeptide of SEQ ID NO:2, as well as fragments thereof, which fragments have at least 20 or 30 contiguous bases, and preferably at least 50 contiguous bases, and to polypeptides encoded by such polynucleotides.

The present invention further relates to a human Pif-1 type helicase polypeptide, which has the deduced amino acid sequence as shown in SEQ ID NO:2, or which has the amino acid sequence encoded by the deposited cDNA, as well as fragments, analogs and derivatives of such polypeptide.

Analogs of the novel human helicase of the present invention are also within the scope of the present invention. Analogs can differ from the naturally occurring human helicase of the present invention in amino acid sequence, either as variants or mutants or as splice variants, or in ways that do not involve sequence, or both. Non-sequence modifications include in vivo or in vitro chemical derivatization of the human helicase of the present invention. Non-sequence modifications include changes in acetylation, methylation, phosphorylation, carboxylation, or glycosylation.

Preferred analogs include the novel human helicase of the present invention (or biologically active fragments thereof) whose sequences differ from the wild-type sequence by one or more conservative amino acid substitutions or by one or more non-conservative amino acid substitutions, deletions or insertions which do not abolish the biological activity of the human helicase of the present invention. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

TABLE 1

Conservative amino acid replacements

For Amino Acid Replace with any of:

| | | |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |

TABLE 1-continued

Conservative amino acid replacements

For Amino Acid Replace with any of:

| | | |
|---|---|---|
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogues within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or ε amino acids.

Other analogues include possible variants of related helicases which contain conserved helicase motifs but may have related and/or overlapping functions, like the pif1 and related RRM3 in yeast.

Other analogues include other higher eukaryotic helicases retrieved by homology to the human helicase sequence by methods that are obvious to those expert in the art [hybridization, data mining, sequence homology searches].

In terms of general utility of the novel human helicase protein of the present invention, as described above, the human helicase of the present invention is useful to screen for modulators of the human helicase, and useful to arrest cell division. The novel nucleic acid sequence of the present invention are also useful for manufacturing human helicase, for gene therapy, and may be incorporated into a host cell or cells.

As discussed above, by "viability" is meant the ability of a cell to divide. Modulators of the activity of a Pif-1 helicase will either increase or decrease the number of cell divisions through which that cell may pass. Such numbers are readily measured by methods well known to those in the art.

In a further aspect, the present invention encompasses a method for treatment of a disease or condition in a patient by identifying a patient suffering from a disease or condition caused by a high or low level of telomerase activity in a cell or cells, and contacting the cell or cells in said patient with a modulator as described above. For example, highly proliferating cancer cells, may be arrested, or senesced, or killed by such an helicase inhibitor.

In an additional aspect, the present invention provides a method of identifying a modulator of human Pif-1 type helicase by contacting a potential modulator with human helicase and assaying the activity of the helicase in vitro or in vivo. Useful modulators include those that specifically increase or decrease the activity of human helicase, and include oligonucleotides, peptides, and/or small molecules which are able to specifically interact with human Pif-1 helicase, with DNA or RNA encoding human helicase, with naturally occurring inhibitors or activators of human helicase, or with DNA or RNA encoding such naturally occurring inhibitors or activators of human helicase.

The gene constructs of the present invention can also be used as part of a gene therapy protocol to deliver nucleic acids encoding the human helicase of the present invention. The invention features expression vectors for in vivo transfection and expression, or overexpression, of a human Pif-1 helicase. Expression constructs of the present invention may be administered in any biologically effective carrier, e.g., any formulation or composition capable of effectively delivering the human helicase gene to cells in vivo. Approaches include insertion of the subject gene in viral vectors including recombinant retroviruses, adenoviruses, adeno-associated viruses, and herpes simplex virus-1, or recombinant bacterial or eukaryotic plasmids. Viral vectors transfect cells directly; an advantages of infection of cells with a viral vector is that a large proportion of the targeted cells can receive the nucleic acid. Several viral delivery systems are known in the art and can be utilized by one practicing the present invention.

In addition to viral transfer methods, non-viral methods may also be employed to cause expression of the human helicase in the tissue of an animal. Most non-viral methods of gene transfer rely on normal mechanisms used by mammalian cells for the uptake and intracellular transport of macromolecules. Exemplary gene delivery systems of this type include liposomal derived systems (like lipofectin, etc), poly-lysine conjugates, Ca-phosphate precipitates, and artificial viral envelopes. DNA of the present invention may also be introduced to cell(s) by direct injection of the gene construct.

In clinical settings, the gene delivery systems for the therapeutic human Pif-1 helicase gene can be introduced into a patient by any of a number of methods, each of which is known in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. Here again viral vectors can also be used for delivery.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced in tact from recombinant cells, e.g., retroviral vectors, the pharmaceutical preparation can comprise one or more cells which produce the gene delivery system.

Another aspect of the invention relates to the use of an isolated nucleic acid in "antisense" therapy. As used herein, "antisense" therapy refers to administration or in situ generation of oligonucleotides or their derivatives which specifically hybridize under cellular conditions, with the cellular mRNA and/or genomic DNA encoding the human Pif-1 helicase of the present invention so as to inhibit expression of the encoded protein, e.g., by inhibiting transcription and/or translation. In general, "antisense" therapy refers to the range of techniques generally employed in the art, and includes any therapy which relies on specific binding to oligonucleotide sequences.

The human Pif-1 helicase as shown in SEQ ID NO:2, and fragments thereof, are also within the scope of Applicants invention. Fragments of the protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Digestion with "end-nibbling" endonucleases can thus generate DNA's which encode an array of fragments. DNA's which encode fragments of the human helicase protein can also be generated by random shearing, restriction digestion, PCR amplification from the cDNA or a combination of the above-discussed methods. These partial DNA fragments can also be used in vectors to express selected regions of the encoded protein, by methods practiced by those skilled in the art. These fragments or the whole protein can be used to generate antibodies for detection of hPif1 protein for diagnostic or clinical purposes.

Protein fragments can also be chemically synthesized using techniques known in the art such as conventional Merrifield solid phase f-Moc or t-Boc chemistry. Amino acid sequence variants of the human helicase protein of the present invention can be prepared by random or directed mutagenesis of DNA which encodes a protein or a particular domain or region of the protein. Useful methods are known in the art, e.g., PCR mutagenesis and saturation mutagenesis. A library of random amino acid sequence variants can also be generated by the synthesis of a set of degenerate oligonucleotides sequences, a process known and practiced by those skilled in the art.

Non-random or directed mutagenesis techniques can be used to provide specific sequences or mutations in specific regions. These techniques can be used to create variants which include, e.g., deletions, insertions, or substitutions of residues of the known amino acid sequence of the human helicase protein of the present invention. The sites for mutation can be modified individually or in series, e.g., by (1) substituting first with conserved amino acids then with more radical choices depending upon results achieved; (2) deleting the target residue; or (3) inserting residues of the same or a different class adjacent to the located site, or a combination of options (1)–(3). Alanine scanning mutagenesis is a useful method for identification of certain residues or regions of a desired protein that are preferred locations or domains for mutagenesis. Oligonucleotide-mediated mutagenesis, cassette mutagenesis, and combinatorial mutagenesis are useful methods for preparing substitution, deletion, and insertion variants of DNA known to those skilled in the art.

Drug screening assays are also provided in the present invention. By making available purified and recombinant human Pif-1 helicase of the present invention, or fragments thereof, one skilled in the art can use the human helicase to screen for drugs which either increase or decrease the activity of human helicase. Generally, any specific helicase assay can be used to identify modulators of human helicase, for example, as described by Lahaye, et al., (1991) EMBO Journal 10:997. The term "modulators" encompasses compounds which increase activity, decrease activity, activate or inactivate the activity or production of human helicase. Modulators encompasses polynucleotides, oligonucleotides (e.g., those useful in antisense therapy as discussed above), peptides, proteins, and small molecules. "Nucleic acids" or "polynucleotides" includes individual nucleotides as well as DNA and RNA sequences or fragments thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as primary screens in that they can be generated to permit rapid development and relatively easy detection of an alteration in a molecular target which is mediated by a test compound.

Also within the scope of the present invention is a process for modulating the human Pif-1 helicase of the present invention, and thereby modulating telomere formation or elongation. The term "modulating" encompasses increasing activity, decreasing activity, activating or inactivating the human helicase of the present invention. Modulating the activity of human helicase is desirable for treating helicase-associated disorders. "Helicase-associated disorders" refers to any disorder or disease state in which human helicase plays a role in the pathway of that disorder or disease, or in which modulation of helicase activity may modify the outcome. Such diseases include, but is not limited to, cellular senescence and tumor growth. As used herein the term "treating" refers to the alleviation of symptoms of a particular disorder in a patient, the improvement of an ascertainable measurement associated with a particular disorder, or the prevention of a particular cellular state (such as cellular senescence or tumor growth).

Modulators of telomere formation or elongation can be identified by contacting a potential modulator of telomere formation or elongation with a human Pif-1 type helicase of the present invention in the presence of cells; and assaying the activity of said human Pif-1 type helicase, wherein said modulator specifically increases or decreases helicase activity and thereby modulates said telomere formation or elongation.

Modulators of human helicase, e.g., small molecules, oligonucleotides or ribozymes, can be administered prophylactically, or to patients suffering from a helicase-associated disorder, e.g., by exogenous delivery of the compound to an infected tissue by means of an appropriate delivery vehicle, e.g., a liposome, a controlled release vehicle, by use of electroporation or ion paired molecules, or covalently attached adducts, and other pharmacologically approved methods of delivery.

The specific delivery route of any selected compound will depend on the use of the compound. Generally, a specific delivery program for each agent will focus on naked compound uptake with regard to intracellular localization, followed by demonstration of efficacy. Alternatively, delivery to these same cells in an organ or tissue can be pursued.

Some methods of delivery, e.g., for polynucleotides, that may be employed include encapsulation in liposomes, transduction by retroviral vectors, conjugation with cholesterol, localization to nuclear compartment utilizing antigen binding sites found on most snRNAs, neutralization of charge of polynucleotides by using nucleotide derivatives, and use of blood stem cells to distribute polynucleotides throughout the body.

Also within the scope of the present invention are pharmaceutical compositions comprising at least one compound capable of modulating the activity of human Pif-1 helicase. The human Pif-1 helicase modulator may be administered alone or with at least one additional active compound, and any pharmaceutically acceptable carrier, adjuvant or vehicle. "Additional active compounds" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with a human Pif-1 modulating compound, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate, surfactants used in pharmaceutical dosage forms such as Tween or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as (-, (- and (-cyclodextrin, or chemically modified derivatives such as hydroxyalkylcyclodextrins, including 2- and 3-hydroxypropyl-(-cyclodextrins, or other solubilized derivatives may also be used to enhance delivery of the compounds of the present invention.

The pharmaceutical compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical compositions comprising at least one human Pif-1 modulating compound of the present invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The pharmaceutical compositions of the present invention may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. Human Pif-1 modulating compounds of the present invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating human Pif-1 modulating compounds with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art. Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

A "therapeutically effective" amount of a human Pif-1 modulating compound of the present invention may be determined by one of ordinary skill in the art, and may be administered in a single dose or in the form of multiple doses. By "therapeutically effective" is meant an amount necessary to achieve a desired result, for example, alleviation of symptoms of a particular disorder in a patient, the improvement of an ascertainable measurement associated with a particular disorder, or the prevention of a particular immune response. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans.

The human Pif-1 modulating compounds of the present invention, as well as pharmaceutical compositions comprising said human Pif-1 modulating compounds, may be employed alone or in combination with each other and/or other suitable therapeutic agents, such as antiinflammatories, antiproliferatives, chemotherapeutic agents, and immunosuppressants.

Disease states which may be treated by human Pif-1 helicase, or human Pif-1 modulating compounds, of the present invention include cellular senescence, cancer and tumors (such as solid tumors, lymphomas and leukemia), breast, lung and prostate cancer, viral replication diseases (including DNA and RNA viral replication diseases, such as retroviral diseases, and herpes), inflammatory responses.

EXAMPLES

The following examples are included for understanding the present invention and are not intended to limit the scope of Applicants invention.

Example 1

Identification of Human Pif-1 Type Helicase

To obtain the full-length sequence, primers were designed based upon sequences of EST clones. 5'-RACE was performed and PCR products from human heart, fetal lung, and fetal thymus cDNAs were subcloned and sequenced. Novel 5' sequences derived from first-round PCR were used in primer design for the next round of 5'-RACE. Three more rounds of 5'-RACE were performed and a potential initiation codon ATG was identified. Database search allowed us to identify a EST clone (I.M.A.G.E. #1335691) which contains most of hpif1 coding sequence. A composite full-length cDNA clone was generated by ligating EST# 1335691 and the 5'-RACE PCR product. The hpif1 gene encodes a polypeptide of 689 amino acids, which is close to the size of the pif-1 of C. elegans (677 amino acids).

As depicted in FIG. 3, the predicted amino acid sequence exhibits strong similarity to the known PIF1 protein sequences from yeast and the nematode C. elegans. Additional evidence of homology is provided by the striking sequence conservation observed in the regions of and surrounding the putative A and B binding motifs and DNA binding site. These regions are believed to be directly involved in the functional activity of pif1.

The isolated nucleic acid sequence overlaps with a number of ESTs and STSs deposited in the public databases (GenBank accession numbers: AA827755, AA464521, AA279102, T85126, AA743647, AA464522, T54683, W60880, G14453, AA278838, T88870, T54599, AA872541, G14858, AA642924, and W60651). None of these nucleotide fragments have been associated with pif1 activity prior to this claim.

Of direct interest, however, is the fact that one of these STSs, SHGC-13832 (GenBank accession number G14958), has been mapped to the D15S117-D15S159 region of human chromosome 15. SHGC-13832 overlaps at the 3'end of the human pif1 gene (see FIG. 2). The sequence identity over this 250 base pair region is greater than 97%. Given the distinctiveness associated with 3' gene sequence regions, this evidence is sufficient to establish the map position of human pif1 within this 8 cM region (between 50.8 and 58.8 cm from the p-telomere of chromosome 15).

The cDNA insert containing the coding region for hpif1 was transcribed by T3 phage RNA polymerase and translated in a reticulocyte cell lysate coupled system [Promega] in the presence of $^{35}S$ methionine. After translation the mixture was boiled and the proteins separated in 10% polyacrylamide gel [Biorad] by electrophoresis at 100 v for 1 hour at room temperature. The gel was dried and the autoradiograph after overnight exposure is shown below. A single band of approximately 80 kDa represents in vitro synthesized hpif1 protein.

The following experimental procedures were used in the above examples: The sequences were determined by using an Applied Biosystems automated sequencer and fluorescent labelled chain terminators, as described by those familiar in the art.

Although the present invention has been described in some detail by way of illustration and example for purposes of clarity and understanding, it will be apparent that certain changes and modifications may be practiced within the scope of the appended claims.

What is claimed is:

1. A purified and isolated nucleic acid molecule comprising a polynucleotide encoding a polypeptide having the amino acid sequence of SEQ ID NO:2 or an active portion of said sequence which exhibits helicase activity.

2. A purified and isolated nucleic acid molecule comprising the nucleotide sequence of SEQ ID NO:1 or a degenerate variant of SEQ ID NO:1.

3. An expression vector comprising the nucleic acid molecule of claim 1.

4. An expression vector comprising the nucleic acid molecule of claim 2.

5. A transformant host cell comprising an expression vector comprising the nucleic acid molecule of claim 1 and an expression control sequence operatively linked to the nucleic acid molecule.

6. A transformant host cell comprising an expression vector comprising the nucleic acid molecule of claim 2 and an expression control sequence operatively linked to the nucleic acid molecule.

7. A purified and isolated nucleic acid molecule comprising the complement of the nucleotide sequence of claim 2.

8. A method of producing a Pif-1 helicase, said method comprising the steps of:
   a) inserting a nucleic acid sequence according to claim 1 encoding said Pif-1 helicase into an appropriate expression vector,
   b) transfecting said expression vector into an appropriate transfection host cell,
   c) growing said transfected host cells in an appropriate culture media, and
   d) purifying the Pif-1 helicase from said culture media.

9. A method of producing a Pif-1 helicase, said method comprising the steps of:
   a) inserting a nucleic acid sequence according to claim 2 encoding said Pif-1 helicase into an appropriate expression vector,
   b) transfecting said expression vector into an appropriate transfection host cell,
   c) growing said transfected host cells in an appropriate culture media, and
   d) purifying the Pif-1 helicase from said culture media.

10. A purified and isolated nucleic acid molecule which encodes a protein that exhibits human Pif-1 helicase activity comprising a nucleic acid sequence selected from the group consisting of:
    a) a nucleic acid sequence encoding a polypeptide having the amino acid sequence of SEQ ID NO:2; and
    b) a nucleic acid sequence having at least 90% sequence identity to (a).

11. A nucleic acid molecule of claim 2 comprising at least 30 contiguous bases of SEQ ID NO:1.

12. A nucleic acid molecule of claim 2 comprising at least 50 contiguous bases of SEQ ID NO: 1.

13. The purified and isolated nucleic acid molecule of claim 1, wherein the polynucleotide encodes a polypeptide comprising an amino acid sequence encoding a human Pif-1 helicase.

14. A purified and isolated nucleic acid molecule comprising a polynucleotide encoding a polypeptide having the amino acid sequence encoded by the cDNA clone contained in ATCC Accession Number 204169.

15. The purified and isolated nucleic acid molecule of claim 14, wherein said polynucleotide encodes a polypeptide having the complete amino acid sequence encoded by the cDNA clone contained in ATCC Accession Number 204169.

16. An isolated nucleic acid which encodes a protein which exhibits human Pif-1 helicase activity comprising a sequence at least 80% identical to SEQ ID NO:1.

17. An isolated nucleic acid comprising a sequence that encodes a polypeptide which exhibits human Pif-1 helicase activity, the amino acid sequence of which is at least 80% identical to SEQ ID NO:2.

* * * * *